(12) United States Patent
Pan

(10) Patent No.: US 8,257,689 B2
(45) Date of Patent: Sep. 4, 2012

(54) ANTIPERSPIRANT ACTIVE COMPOSITIONS HAVING SEC CHROMATOGRAM EXHIBITING HIGH SEC PEAK 4 INTENSITY

(75) Inventor: Long Pan, Cherry Hill, NJ (US)

(73) Assignee: Colgate-Palmolive Company, New York, NY (US)

( * ) Notice: Subject to any disclaimer, the term of this patent is extended or adjusted under 35 U.S.C. 154(b) by 275 days.

(21) Appl. No.: 12/446,045

(22) PCT Filed: Dec. 12, 2008

(86) PCT No.: PCT/US2008/086556
§ 371 (c)(1),
(2), (4) Date: Apr. 17, 2009

(87) PCT Pub. No.: WO2009/076591
PCT Pub. Date: Jun. 18, 2009

(65) Prior Publication Data
US 2010/0303749 A1 Dec. 2, 2010

Related U.S. Application Data

(63) Continuation-in-part of application No. PCT/US2007/087145, filed on Dec. 12, 2007.

(51) Int. Cl.
*A61K 8/28* (2006.01)
*A61K 8/26* (2006.01)
*A61K 8/58* (2006.01)

(52) U.S. Cl. .................................. 424/66; 424/68

(58) Field of Classification Search .................. 424/66
See application file for complete search history.

(56) References Cited

U.S. PATENT DOCUMENTS

| | | | |
|---|---|---|---|
| 3,979,510 A | 9/1976 | Rubino | |
| 3,991,176 A | 11/1976 | Rubino | |
| 4,871,525 A | 10/1989 | Giovanniello et al. | |
| 4,900,534 A | 2/1990 | Inward | |
| 5,330,751 A | 7/1994 | Curtin et al. | |
| 5,348,720 A | 9/1994 | Vincenti et al. | |
| 5,358,694 A | 10/1994 | Giovanniello | |
| 5,643,558 A | 7/1997 | Provancal | |
| 5,705,171 A | 1/1998 | Iovanni et al. | |
| 5,997,850 A | 12/1999 | Tang et al. | |
| 6,010,688 A * | 1/2000 | Shen ........................ | 424/66 |
| 6,066,314 A | 5/2000 | Tang et al. | |
| 6,074,632 A | 6/2000 | Shen | |
| 6,136,302 A | 10/2000 | Juneja et al. | |
| 6,149,897 A | 11/2000 | Swaile | |
| 6,245,325 B1 | 6/2001 | Shen | |
| 6,342,210 B1 | 1/2002 | Cai et al. | |
| 6,375,937 B1 | 4/2002 | Chopra et al. | |
| 6,436,381 B1 | 8/2002 | Carrillo et al. | |
| 6,726,901 B2 | 4/2004 | Yin et al. | |
| 6,835,373 B2 | 12/2004 | Kolodzik et al. | |
| 6,902,724 B1 | 6/2005 | Parekh et al. | |
| 6,936,242 B2 | 8/2005 | Elliott et al. | |
| 6,942,850 B2 | 9/2005 | Coe et al. | |
| 6,969,510 B2 | 11/2005 | Holerca et al. | |
| 7,105,691 B2 | 9/2006 | Holerca et al. | |
| 7,189,387 B2 | 3/2007 | Chuah et al. | |
| 7,229,611 B2 | 6/2007 | Zamudio-Tena et al. | |
| 7,256,875 B2 | 8/2007 | Maier et al. | |
| 2004/0265255 A1 | 12/2004 | Holerca et al. | |
| 2005/0265939 A1 | 12/2005 | Li | |
| 2006/0153788 A1 | 7/2006 | Swaile et al. | |
| 2006/0204463 A1 | 9/2006 | Tang et al. | |
| 2006/0292098 A1 | 12/2006 | Scavone et al. | |
| 2007/0003499 A1 | 1/2007 | Shen et al. | |
| 2007/0020211 A1 | 1/2007 | Li et al. | |
| 2007/0110687 A1 | 5/2007 | Mattai et al. | |
| 2007/0196302 A1 | 8/2007 | Pratt et al. | |
| 2007/0196303 A1 | 8/2007 | Li et al. | |

FOREIGN PATENT DOCUMENTS

| | | |
|---|---|---|
| CA | 2445924 | 5/2004 |
| GB | 2144992 | 8/1984 |
| WO | WO 2006/103092 | 10/2006 |
| WO | WO 2009/075678 | 6/2009 |
| WO | WO 2009/076591 | 6/2009 |

OTHER PUBLICATIONS

International Search Report PCT/US2008/086556 Mailed Apr. 6, 2009.
Search report from PCT/US2008/086556 mailed Apr. 6, 2009.
International Search Report for International Application No. PCT/US2007/087145 mailed Apr. 6, 2009.
Chen et al., 2006, "Evaluation of $Al_{30}$ Polynuclear Species in Polyaluminum Solutions As Coagulant for Water Treatment," Chemosphere 64(6)912-918.
Chen et al., 2009, "On the Acid-Base Stability of Keggin $Al_{13}$ and $Al_{30}$ Polymers in Polyaluminum Coagulants," J. Mater. Sci. 44:3098-3111.
Huang et al., 2006, "Separation and Purification of Nano-$Al_{13}$ by UF Method," Colloids and Surfaces A: Physicochem, Eng. Aspects 275:200-208.

(Continued)

*Primary Examiner* — Robert A Wax
*Assistant Examiner* — Jessica Worsham
(74) *Attorney, Agent, or Firm* — Michael F. Morgan

(57) ABSTRACT

An antiperspirant active composition comprising an aluminum salt having an aluminum to chloride molar ratio of about 0.3:1 to about 3:1, exhibiting a SEC chromatogram having a SEC Peak 4 to Peak 3 intensity ratio of at least 16 and a Peak 4 intensity greater than a Peak 5 intensity in aqueous solution. The composition can optionally include zirconium. Also, methods and processes of making the same.

42 Claims, 15 Drawing Sheets

OTHER PUBLICATIONS

Shen, 1998, "Synthesis and Speciation of Polyaluminum Chloride for Water Treatment," Environment International 24(8):899-910.

Zhang et al., 2008, "Coagulation Characteristics of Polyaluminum Chlorides PAC-$Al_{30}$ on Humic Acid Removal from Water," Separation and Purification Technology 63:642-647.

Allouche et al., 2000, "$Al_{30}$: A Giant Aluminum Polycation," Agnew. Chem. Int. Ed. Engl. 39(3):511-514.

Allouche et al., 2003, "Conversion of $Al_{13}$ Keggin $\epsilon$ into $Al_{30}$: A Reaction Controlled by Aluminum Monomers," Inorganic Chemistry Communications 6:1167-1170.

Bottero, 1980, "Studies of Hydrolized Aluminum Chloride Solutions, 1. Nature of Aluminum Species and Composition of Aqueous Solutions," The Journal of Physical Chemistry 84:2933-2939.

Casey, 2005, "Large Aqueous Aluminum Hydroxide Molecules," Chemical Reviews 106(1):1-16.

Chen et al., 2007, "Effect of Thermal Treatment on the Formation and Transformation of Keggin $Al_{13}$ and $Al_{30}$ Species in Hydrolytic Polymeric Aluminum Solutions," Colloids and Surfaces A: Physicochem. Eng. Aspects 292:110-118.

Fu et al., 1991, "Aging Processes of Alumina Sol-Gels: Characterization of New Aluminum Polyoxycations by $^{27}Al$ NMR Spectroscopy," Chem. Mater. 3:602-610.

Roswell et al., 2000, "Speciation and Thermal Transformation in Alumina Sols: Structures of the Polyhydroxyoxoaliminum Cluster $[Al_{30}O_8(OH)_{56}(H_2O)_{26}]^{18+}$ and Its $\delta$-Keggin Moieté," J. Am. Chem. Soc. 122:3777-3778.

Shafran et al., 2005, "The Static Anion Exchange Method for Generation of High Purity Aluminum Polyoxocations and Monodisperse Aluminum Hydroxide Nanoparticles," J. Materials Chemistry 15:3415-3423.

U.S. Appl. No. 12/531,145, filed Sep. 14, 2009.

File History from U.S. Appl. No. 12/531,145 through Oct. 20, 2011.

Rosenberg, Allan H., Ph.D., "Antiperspirant Actives—Enhanced Efficacy Aluminum-Zirconium-Glycine (AZG) Salts" (Cosmetics and Toiletries Worldwide, Fondots, D. C. ed., Hartfordshire, UK: Aston Publishing Group, 1993, pp. 252, 254-256).

Rosenberg, Allan H., Ph.D., "New Antiperspirant Salt Technology," (Cosmetics and Toiletries Manufacture Worldwide, Fondots, D. C. ed., Hartfordshire, UK: Aston Publishing Group).

* cited by examiner

US 8,257,689 B2

ANTIPERSPIRANT ACTIVE COMPOSITIONS HAVING SEC CHROMATOGRAM EXHIBITING HIGH SEC PEAK 4 INTENSITY

CROSS REFERENCE TO RELATED APPLICATIONS

This application is a continuation in part of International Application No. PCT/US2007/87145, filed on 12 Dec. 2007, which is incorporated herein by reference.

BACKGROUND OF THE INVENTION

Antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) of 100-500,000. It has been clinically shown that, in general, the smaller the species, the higher the efficacy for reducing sweat.

In an attempt to increase the quality and quantity of smaller aluminum and/or zirconium species, a number of efforts have focused on: (1) how to select the components of ACH and ZAG that affect the performance of these materials as antiperspirants; and (2) how to manipulate these components to obtain and/or maintain the presence of smaller types of these components. These attempts have included the development of analytical techniques to identify the components. Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species can be detected in commercial ACH and ZAG complexes appearing in a chromatogram as peaks 1, 2, 3, 4 and a peak known as "5,6". Peak 1 is the larger Zr species (greater than 60 Angstroms). Peaks 2 and 3 are larger aluminum species. Peak 4 is smaller aluminum species (aluminum oligomers, or small aluminum cluster) and has been correlated with enhanced efficacy for both Al and Al/Zr salts. Peak 5, 6 is the smallest aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots, D. C. Hartfordshire, UK; Aston Publishing Group, 1993, pages 252, 254-256).

Attempts to activate antiperspirant salts to produce materials having improved efficacy have included developing processes for obtaining composition having large amounts of Peak 4 species. None of these efforts, however, have resulted in an antiperspirant composition having a composition with little or no Peak 3 and optionally little or no Peak 5.

BRIEF SUMMARY OF THE INVENTION

The present invention provides for an antiperspirant active composition comprising an aluminum salt having an aluminum to chloride molar ratio of about 0.3:1 to about 3:1, exhibiting a SEC chromatogram having a SEC Peak 4 to Peak 3 intensity ratio of at least 7 and a Peak 4 intensity greater than a Peak 5 intensity in aqueous solution, and optionally including zirconium.

The present invention also provides for a method of making an antiperspirant active composition that exhibits a SEC chromatogram having a SEC Peak 4 to Peak 3 intensity ratio of at least 7 and a Peak 4 intensity greater than a Peak 5 intensity in aqueous solution comprising:

I) heating an aqueous solution containing an aluminum salt having an aluminum to chloride molar ratio of about 0.3:1 to about 3:1, optionally with a buffer agent, at a temperature of about 50° C. to about 95° C. to reflux for a period of time of about 1 hour to about 5 hours to obtain an aluminum salt solution;

II) adding an aqueous solution of an inorganic base to obtain an aluminum salt solution having an OH:Al molar ratio of about 2:1 to about 2.6:1 to obtain a pH adjusted aluminum salt solution having a pH of about 2 to about 5; and III) optionally adding an aqueous solution containing a zirconium compound to the pH adjusted aluminum salt solution to thereby obtain an aluminum-zirconium salt solution having a molar ratio of aluminum to zirconium of about 5:1 to about 10:1.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

DETAILED DESCRIPTION OF THE INVENTION

Figure 1:
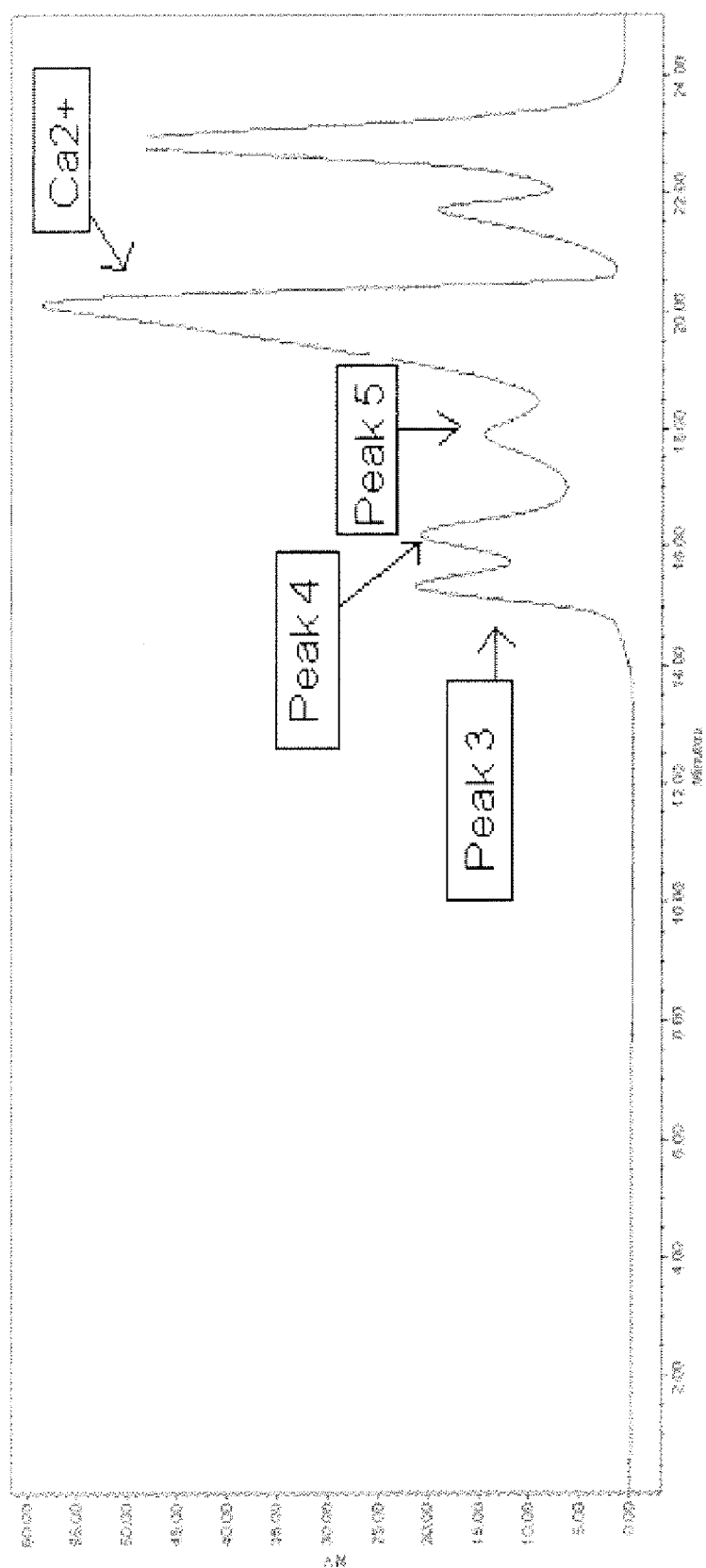
FIG. 1 illustrates an SEC chromatogram of a prior art antiperspirant active composition.

As used throughout, ranges are used as a shorthand for describing each and every value that is within the range. Any value within the range can be selected as the terminus of the range.

The present invention is directed to an antiperspirant active composition having a high SEC peak 4 in aqueous solution. The composition is obtained by a stepwise procedure to neutralize aluminum chloride in a solution (optionally buffered) using inorganic bases. In some embodiments, the antiperspirant active compositions obtained by this stepwise procedure include aluminum salts having an aluminum to chloride molar ratio of about 0.3:1 Co about 3.1 the aluminum a salt has a SEC Peak 4 to Peak 3 intensity ratio of at least 7 and a Peak 4 intensity greater than a Peak 5 intensity in aqueous solution. The composition may optionally include zirconium.

Optionally, a buffer can be included. Buffers that can be used can be chosen from amino acids, glycine, and betaine. The buffer to aluminum molar ratio in certain embodiments can be about 0.1:1 to about 3:1. In another embodiment, the buffer to aluminum molar ratio is about 0.5:1 to about 2:1. In another embodiment, the buffer aluminum molar ratio is about 1:1 to about 1.5:1.

The compositions may be made in a variety of ways involving a stepwise procedure to neutralize aluminum chloride. In solution (optionally buffered) using inorganic basic salts. The procedure generally includes the step of heating an aqueous solution containing an aluminum chloride compound (optionally with a buffer agent) at a temperature of about 50° C. to about 95° C. to reflux for a period of time of about 1 hour to about 5 hours. In one such embodiment, an aqueous solution containing an aluminum chloride compound is heated at a temperature of about 75° C. to about 95° C. to reflux for a period of time of about 3 hours to about 4 hours. In another such embodiment, an aqueous solution containing an aluminum chloride compound and a buffer agent is heated at a temperature of about 75° C. to about 95° C. to reflux for a period of time of about 3 hours to about 4 hours. In one embodiment, the temperature is about 85° C.

In some embodiments, the solution has a buffer agent to aluminum molar ratio of about 0.1:1 to about 3:1. To adjust the pH of the aluminum salt solution, an aqueous solution of an inorganic base is added to the heated solution to thereby obtain a pH adjusted aluminum salt solution having a hydroxide to aluminum molar ratio of about 1:1 to about 4:1, and a pH of about 2 to about 5. In one such embodiment, the hydroxide to aluminum molar ratio of about 2:1 to about 3:1. In another such embodiment, the hydroxide to aluminum molar ratio is about 2.1:1 to about 2.6:1.

In some embodiments, a zirconium salt may also be added to the pH adjusted aluminum salt solution. In one other such embodiment, the molar ratio of Al:Zr is about 5:1 to about 10:1. The antiperspirant active composition has a SEC Peak 4 to Peak 3 intensity of at least 7 and a Peak 4 intensity greater than a Peak 5 intensity in aqueous solution.

In one embodiment, an aqueous aluminum chloride salt solution is buffered with betaine monohydate and held at about 50° C. to about 95° C. to reflux for a period time of about 1 to about 6 hours. To the heated solution, an aqueous solution of an inorganic base is added dropwise over a period of time of about 1 to about 3 hours while maintaining the aluminum-betaine solution at about 50° C. to about 95° C. to reflux, in one such embodiment, the solution has a betaine; to aluminum molar ratio of about 1.1. In another such embodiment, the solution has a betaine to aluminum molar ratio of about 1.25.

In one embodiment, an aqueous solution containing an aluminum chloride compound is buffered with betaine monohydrate and held at about 75° C. to about 95° C. to reflux for a period of time of about 3 hours to about 4 hours. In another such embodiment, an aqueous solution of an inorganic base is added dropwise over a period of time of about 1 to about 3 hours while maintaining the aluminum-betaine solution at about 75° C. to about 95° C. to reflux. In another embodiment, an aqueous solution of an inorganic base is added over a period of time in a series of additions while maintaining the aluminum-betaine solution at about 75° C. to about 95° C. to reflux. In one such embodiment, the inorganic base is added in at least 3 additions. In another such embodiment, the inorganic base is added in at least 5 additions. In another embodiment, a $ZrOCl_2$ solution is added to the pH adjusted aluminum-betaine solution. In one such embodiment, the molar ratio of Al:Zr is about 8. In another such embodiment, the molar ratio of Al:Zr is about 7. In one other such embodiment, the molar ratio of Al:Zr is about 9.

In another embodiment, an aqueous aluminum chloride solution is buffered with glycine and held at about 50° C. to about 95° C. to reflux for a period time of about 1 to about 6 hours. To the heated solution, an aqueous solution of an inorganic base is added dropwise over a period of time of about 1 to about 3 hours while maintaining the aluminum-glycine solution at about 50° C. to about 95° C. to reflux. In one such embodiment, the solution has an aluminum to glycine molar ratio of about 0.4. In another such embodiment, the solution has an aluminum to glycine molar ratio of about 0.8.

In another embodiment, an aqueous solution containing an aluminum chloride compound is buffered with glycine and held at about 75° C. to about 95° C. to reflux for a period of time of about 3 hours to about 4 hours. In another such embodiment, an aqueous solution of an inorganic base is added dropwise over a period of time of about 1 to about 3 hours while maintaining the aluminum-glycine solution at about 75° C. to about 95° C. to reflux. In another embodiment, an aqueous solution of an inorganic base is added over period of time in a series of additions while maintaining the aluminum-glycine solution at about 75° C. to about 95° C. to reflux. In one such embodiment, the inorganic base is added in at least 3 additions. In another such embodiment, the inorganic base is added in at least 5 additions. In one embodiment, the inorganic base is calcium hydroxide. In one such embodiment, the addition of calcium hydroxide provides an aqueous solution having a $Ca(OH)_2$:glycine molar ratio of about 1.25:1 to about 1:1.

In another embodiment, a $ZrOCl_2$ solution is added to the pH adjusted aluminum-glycine solution. In one such embodiment, the molar ratio of Al:Zr is about 8. In another such embodiment, the molar ratio of Al:Zr is about 7. In one other such embodiment, the molar ratio of Al:Zr is about 9.

For the above methods, the aluminum chloride salt and inorganic base may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

In one embodiment, the inorganic base can be at least one base chosen from metal hydroxides, calcium hydroxide, strontium hydroxide, sodium hydroxide, barium hydroxide, metal oxides, calcium oxide, strontium oxide, and barium oxide.

The present invention provides for aluminum antiperspirant active compositions and/or aluminum-zirconium antiperspirant active compositions having high levels of low molecular weight Al and Zr species. As illustrated in FIGS. 2 to 7, the high levels of low molecular weight Al and Zr species is reflected in a SEC trace that has an intense Peak 4, low Peaks 1, 2, 3 and 5. The polymerization of the antiperspirant actives in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. Data for Tables in the examples was obtained using an SEC chromatogram using the following parameters: Waters®600 analytical pump and controller, Rheodyne® 77251 injector, Protein-Pak® 125 (Waters) column, Waters 2414 Refractive Index Detector. 5.56 mM nitric acid mobile phase, 0.50 mL/min flow rate, 2.0 microliter injection volume. Data was analyzed using Water® Empower software (Waters Corporation, Milford, Mass.). The concentration of the antiperspirant in solution does not affect the retention time in the machine.

The design of modern AP salts aims at actives with high levels of low molecular weight Al and Zr species, which is reflected in a SEC trace that has intense Peak 4 and low Peaks 1, 2, and 3. Throughout the present study, the levels of the species corresponding to these peaks are estimated based on the following ratios (or percentages):

$$f_{Pi} = \frac{Pi}{\sum Pj} \quad i = 1, 2, 3, 4, 5; \quad j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred antiperspirant salt would have a very low $f_{P1}$, $f_{P2}$, $f_{P3}$, and/or $f_{P5}$, and a high $f_{P4}$.

in certain embodiments, the ratio of Peak 4 to Peak 3 is at least 8, 9, 10, 11, 12, 13, 14, 15, 16, 17, 18, 19, 20, 25, 30, 35, 40, 45, 50, 60, 70, 80, 90, 100, or any number up to infinity.

In one embodiment, an aluminum salt and/or aluminum-zirconium salt, in aqueous solution, exhibit a SEC profile wherein the SEC Peak 4 to Peak 3 intensity ratio is at least 7. In such embodiments, the percentage of SEC Peak 4 of a total area of Peaks 1, 2, 3, 4, 5, and 6 in the SEC chromatogram is: at least 50%; at least 60%; at least 70%; at least 80%; at least 90%, or 95 to 100%. In another such embodiment, the SEC Peak 4 area is 100%.

In another embodiment, the aluminum salt and/or the aluminum-zirconium salt, in aqueous solution, exhibits a SEC profile wherein the SEC Peak 4 to Peak 3 intensity ratio is at least 7 and exhibits low percentage of SEC Peak 3. In such embodiments, the composition has the percentage of SEC Peak 3 area of a total area of Peaks 1, 2, 3, 4, 5, and 6 in the SEC chromatogram is: less than about 1.0%; less than about 5%; less than about 2%; less than about 1%; less than about 0.9%; less than about 0.8%; less than about 0.7%; less than about 0.6%; of less than about 0.5%; less than about 0.4%; less than about 0.3%; less than about 0.2%; or less than about 0.1%. In another such embodiment, the composition has no SEC Peak 3 area.

In another embodiment, the aluminum salt and/or the aluminum-zirconium salt, in aqueous solution, exhibits a SEC profile wherein the SEC Peak 4 to Peak 3 intensity ratio is at least 7 and exhibits low percentages of SEC Peak 5. In such embodiments, the percentage of SEC Peak 5 of a total area of Peaks 1, 2, 3, 4, 5, and 6 in the SEC chromatogram is: less than about 30%; less than about 20%; less than about 10%; less than about 5%; or less than about 1%. In another such embodiment, the composition has no SEC Peak 5 area.

In another embodiment, the aluminum salt and/or the aluminum-zirconium salt, in aqueous solution, exhibits a SEC profile wherein the SEC Peak 4 to Peak 3 ratio is at least and exhibits a low percentage of SEC Peak 1 and a low percentage of SEC Peak 2. In such embodiment, the percentage of SEC Peak 1 area of a total area of Peaks 1, 2, 3, 4, 5, and 6 the SEC chromatogram is: less than about 10%; a SEC Peak 1 area less than about 5%; less than about 2%; less than about 1 less than about 0.9%; less than about 0.8%; of less than about 0.7%: less than about 0.6%; less than about 0.5%; less than about %; less than about 0.3%; less than about 0.2%; or less than about 0.1%. In another embodiment, the complex has no SEC Peak 1 area. In another embodiment, the percentage of SEC Peak 2 area of a total area of Peaks 1, 2, 3, 4, 5, and 6 in the SEC chromatogram is: less than about 10%; less than about 5%; less than about 2%; less than about 1%; less than about 0.9%; less than about 0.8%; less than about 0.7%; less than about 0.6%; less than about 0.5%; less than about 0.4%; less than about 0.3%; less than about 0.2%; or less than about 0.1%. In another embodiment, the composition has no SEC Peak 2 area.

The aluminum antiperspirant active compositions and/or aluminum-zirconium antiperspirant active compositions may be used in a variety of antiperspirant products. If the product is used as a solid powder, the size of the particles of antiperspirant active of the invention can be any desired size, and may include conventional sizes such as in the range of 2 to 100 microns, with selected grades having an average particle size of 30-40 microns; finer sized grades having an average particle size distribution of 2-10 microns with an average size of about 7 microns as made by a suitable dry-grinding method; and micronized grades having an average particle size of less than about or equal to 2 microns, or less than about or equal to 1.5 microns.

The compositions of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition.

Examples of Suitable Formulations

Sticks

Stick products may be made with conventional gelling agents such as stearyl alcohol and dibenzylidene sorbitol. A sample formulation is as follows:

40-55% (particularly 45%);
cyclomethicone (especially D5 cyclomethicone);
20-30% (particularly 21%);
stearyl alcohol 7-15% (particularly)
talc 15-22% (particularly 22%);
antiperspirant active of the invention in particle form; and
1-3% (particularly 2%) fragrance.

Roll Ons

Roll Ons having a sample formulation:

45-65% (particularly 55%) cyclomethicone (especially D5 cyclomethicone);

0.1-10% (particularly 3%) cyclomethicone/dimethicone copolyol (such as Dow Corning 2-5185C) 10-25% (particularly 20%);

antiperspirant active of the invention in solution form (25-45% actives on an anhydrous basis in water);

5-30% (particularly 20%) water; and 1-3% (particularly 2%) fragrance.

Soft Solids

Soft solids may be made with formulations described in U.S. Pat. No. 6,682,749. A sample formulation is as follows:

40-70% (particularly 50%) elastomer in cyclomethicone (KSG-15 from Shin-Etsu);

5-15% (particularly 6%) polyethylene (for example, beads having a density in the range of 0.91-098 g/cm$^3$ and an average particle size in the range of 5-40 microns);

10-20% (particularly 15%) C12-15 alkylbenzoate (FINSOLV™ TN from Finetex);

0.1-25%% (particularly 22%) antiperspirant active of the invention in powder form;

1-15% (particularly 5%) dimethicone (particularly with a viscosity of 100 centistokes); and 1-3% (particularly 2%) fragrance.

Gels

Gels may be made with a variety of formulations such as:

5-50% (particularly 29%) cyclomethicone (particularly D5);

0.1-10% (particularly 3%) cyclomethicone dimethicone copolyol (such as Dow Corning 2-5185C);

0-10% (particularly 5%) polyisobutene 250;

0-10% (particularly 5 of C12-15 alkylbenzoate (FINSOLV™ TN from Finetex);

0-10% (particularly 5%) dimethicone (particularly with a viscosity of 100 centistokes);

0.1-25% (particularly 2.0%) antiperspirant active cif the invention in powder form or 10-25% ((particularly 20%) of active in solution (25-45% actives on an anhydrous basis);

5-50% (particularly 30%) water; and 1-3% (particularly 2%) fragrance.

Note that in the explanation of the invention, where water is listed it is intended to count the contribution of the water present in the antiperspirant solution as part of the overall water content. Thus, water is sometimes listed as part of the actives solution or sometimes listed separately.

In one embodiment the refractive indices of the external and internal phases are matched within 0.005 to obtain a clear product.

Other Formulations of Interest

Formulation A 0.5-2.5% dimethicone copolyol (for example, Dow Corning 2-5185 C (48%));

55-65% elastomer in cyclomethicone (for example, DC-9040 from Dow Corning Corporation (Midland, Mich.) or KSG-15 from Shin-Etsu Silicones of America (Akron, Ohio));

1-10% PPG-3 myristyl ether;

10-25% antiperspirant active of the invention;

10-25% water; and 0.5-1.5% fragrance.

Formulation B 1.0-3.0% dimethicone copolyol (for example, Dow Corning 2-5185C (48%)) 40-60% elastomer in cyclomethicone (for example, DC-9040 from DowCorning Corporation (Midland, Mich.) or KSG-15 from Shin-Etsu Silicones of America (Akron, Ohio));

1-5% cyclomethicone addition to that found in the elastomer);

4-12% PPG-3 myristyl ether:

15-30% antiperspirant active of the invention;

15-35% water; and 0.5-1.5% fragrance.

Formulation C 1.0-3.0% dimethicone copolyol example, Dow Corning 2-5185 C (48%)), 1-10% hydrogenated polyisobutene (for example, Fancol™. Polyiso 250):

40-55% elastomer in cyclomethicone (for example, DC-9040 from Dow Corning Corporation (Midland, Mich.) or KSG-15 from Shin-Esu Silicones of America (Akron, Ohio)).

3-8% PPG-3 myristyl ether;

15-?0% antiperspirant active of invention;

20-30% water; and 1.0-3.0% fragrance.

Formulation D 1.0-3.0% dimethicone copolyol (for example, Dow Corning 2-5185 C (48%)):

40-60% elastomer in cyclomethicone (for example, DC-9040 from Dow Corning Corporation (Midland. Mich.) or KSG-15 from Shin-Esu Silicones of America (Akron, Ohio));

3-8% PPG-3 myristyl ether;

15-30% antiperspirant active of the invention;

15-30% water;

0.5-1.5% fragrance; and 1-10% diethylhexyl naphthalate

Formulation F 0.5-2.5% dimethicone copolyol (for example, Dow Corning 2-5185C (48%));

60-70% elastomer in cyclomethicone (for example, DC-9040 from Dow Corning, Corporation (Midland, Mich.) or KSG-15 from Shin-Etsu Silicones of America (Akron, Ohio));

7-10% antiperspirant active of the invention;

25-35% water;

1-10% methylpropylene diol (MPDiol); and 0.5-1.5% fragrance

Formulation F 1.0-3.0% dimethicone copolyol (for example, Dow Corning 2-5185 C (48%)); 6-10% hydrogenated polyisobutene (for example. FANCOL™ Polyiso 250);

35-45% elastomer in cyclomethicone (for example, DC-9040 from Dow Corning Corporation (Midland, Mich.) or KSG-15 from Shin-Esu Silicones of America (Akron, Ohio));

6-10% PPG-3 myristyl ether;

40-50% antiperspirant active of the invention as 43% active in water no additional water; and 0.5-1.0% fragrance.

Formulation G 0.1-0.6% dimethicone copolyol (for example, Dow Corning 2-5185 C (48%));

4-7% hydrogenated polyisobutene (for example. FANCOL™ Polyiso 250);

40-50% elastomer in cyclomethicone (for example. DC-9040 from Dow Corning Corporation (Midland, Mich.) or KSG-15 from Shin-Etsu Silicones of America (Akron, Ohio));

4-7% PPG-3 myristyl ether;

40-50% antiperspirant active of the invention as 43% active water no additional water; and 0.5-1.0% fragrance.

Formulation H
- 0.5-2.0% dimethicone copolyol (for example, Dow Corning 2-5185 C (48%));
- 1-7% hydrogenated polyisobutene (for example, FANCOL™ Polyiso 250);
- 40-50% elastomer in cyclomethicone (for example, DC-9040 from Dow Corning Corporation (Midland, Mich.) or KSG-15 from Shin-Etsu Silicones of America (Akron, Ohio));
- 45-55% antiperspirant active as 43% active of the invention in water no additional water; and
- 0.5-1.5% fragrance.

Formulation I
- 2-7% dimethicone copolyol (for example, Dow Corning 2-5185 C (48%)),
- 0.1-1% Oleath-20 1-5% C12-15 alkyl benzoate (FINSOLV™ TN);
- 15-25% elastomer in cyclomethicone (for example, DC-9040 from Dow Corning Corporation (Midland, Mich.) or KSG-15 from Shin-Etsu Silicones of America (Akron, Ohio));
- 15-25% antiperspirant active of the present invention;
- 15-30% water; and
- 0.5-1.5% fragrance The cosmetic composition according to the present invention can be packaged conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass there through. Within the context of the present invention, a gel or stick is deemed to be transparent or clear if the maximum transmittance of light of any wavelength in the range 400-800 nm through a sample 1 cm thick is at least 35%, or at least 50%. The gel or liquid is deemed translucent if the maximum transmittance of such light through the sample is between 2% and less than about 35%. A gel or liquid is deemed opaque if the maximum transmittance of light is less than about 2%. The transmittance can be measured by placing a sample of the aforementioned thickness into a light beam of a spectrophotometer whose working range includes the visible spectrum, such as a Bausch & Lomb Spectronie 88 Spectrophotometer. As to this definition of clear, see European Patent Application Publication No. 291,334 A2. Thus, according to the present invention, there are differences between transparent (clear translucent and opaque compositions.

EXAMPLES

Comparative Examples

A 0.72 M $AlCl_3.6H_2O$ (18 mmol) is held at 90° C. and stirred vigorously. To this solution, a 4 N $Ca(OH)_2$ (20 mmol) is added dropwise over a 1 hour 30 minute period. A ratio of OH:Al of 2.22 is employed in an attempt to prevent the formation of larger unwanted Al species. The pH after the reaction was 2.36 due to the low OH:Al ratio. The SEC chromatogram, illustrated in FIG. 1, exhibits multiple peaks including, SEC-Peak 4, and SEC-Peak 5 indicating multiple Al species are present in solution. At a retention time of approximately 15.5 minutes, SEC-Peak 3 is observed due to no buffer betaine or glycine) as control.

Also for comparison, 10% solutions are prepared from commercially available antiperspirants. The solutions are prepared by adding 1 g of antiperspirant to 9 g of water and mixing. The antiperspirant salts were Reach™ 103, Reach™ 301 from Reheis, and Summit™ Z576 from Summit Research Labs.

Example 1

Figure 2:
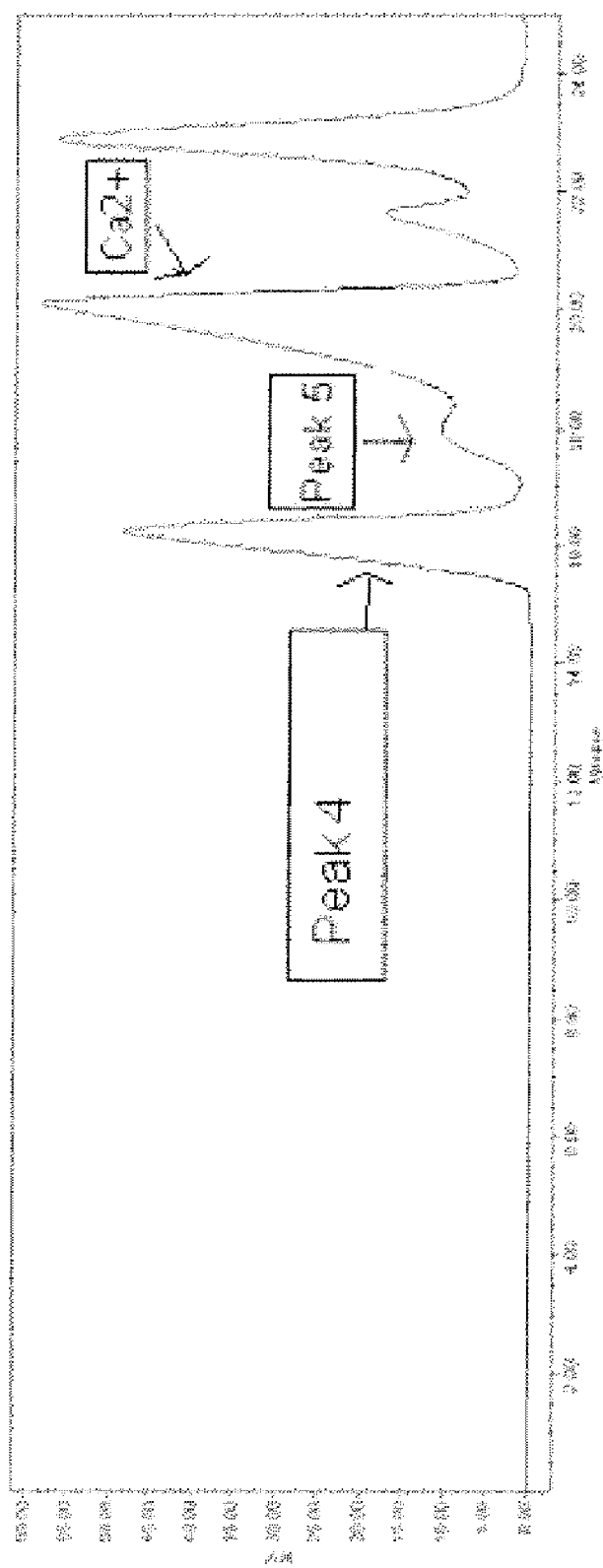
FIG. 2 illustrates an SEC chromatogram having exclusive peaks 4 and 5 for an inventive product, Example 1, of the present invention.

A 0.72 M $AlCl_3.6H_2O$ (18 mmol) is buffered with 20 mmol betaine monohydrate, held at 90° C., and stirred vigorously. To this solution, a 4 N $Ca(OH)_2$ (20 mmol) is added dropwise over a 1 hour 30 minute period. A ratio of OH:Al of 2.22 is employed in an attempt to prevent the formation of large Al species. The pH after the reaction is 2.56 due the low OH:Al ratio. As illustrated in FIG. 2, the SEC chromatogram shows exclusively SEC-Peak 4 and SEC-Peak 5, which are known to represent active anti-perspirant species. Substantially no SEC-Peak 3 species is observed at a retention time of approximately 15.5 minutes.

Example 2

Figure 3:
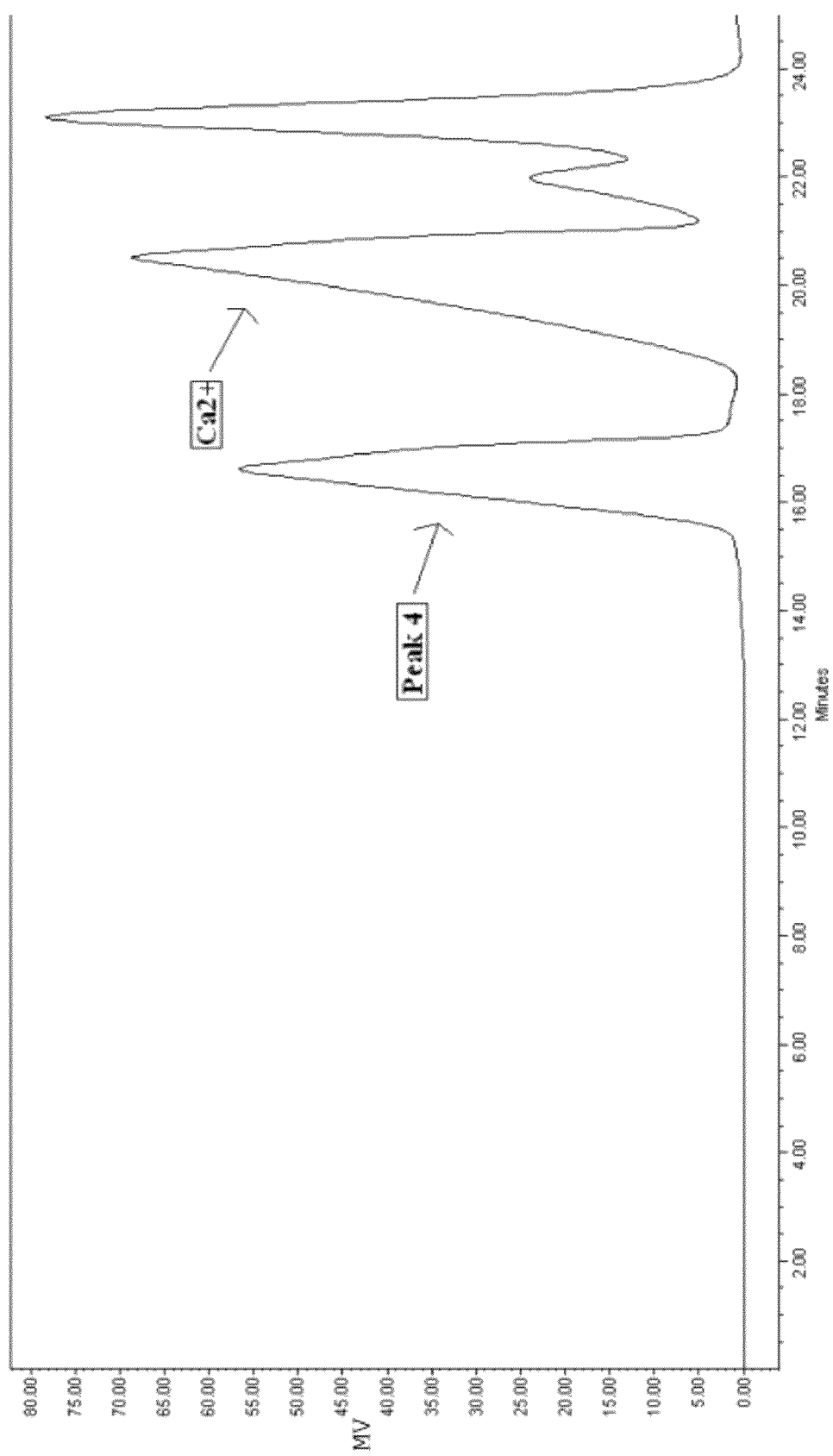
FIG. 3 illustrates an SEC chromatogram having exclusive peak 4 for an inventive product. Example of the present invention.

A 0.72 M $AlCl_3.6H_2O$ (16.26 mmol) was buffered with 20 mmol anhydrous betaine, held at 90° C., and stirred vigorously. To this solution, a 4 N Ca $(OH)_2$ (20 mmol) was added dropwise over a 2 hour period. A ratio of OH:Al of 2.46 was employed in an attempt increase the final pH and to reduce SEC-Peak 5 species. Because a higher OH:Al ratio was used, the addition of the base was extended over a 2 hour period. The pH after the reaction was 4.8. As illustrated in FIG. 3, the SEC chromatogram indicated that the solution contained exclusively SEC-Peak 4 antiperspirant active species. Substantially no SEC-Peak 3 species was observed at a retention time of approximately 15.5 minutes.

Example 3

Figure 4:
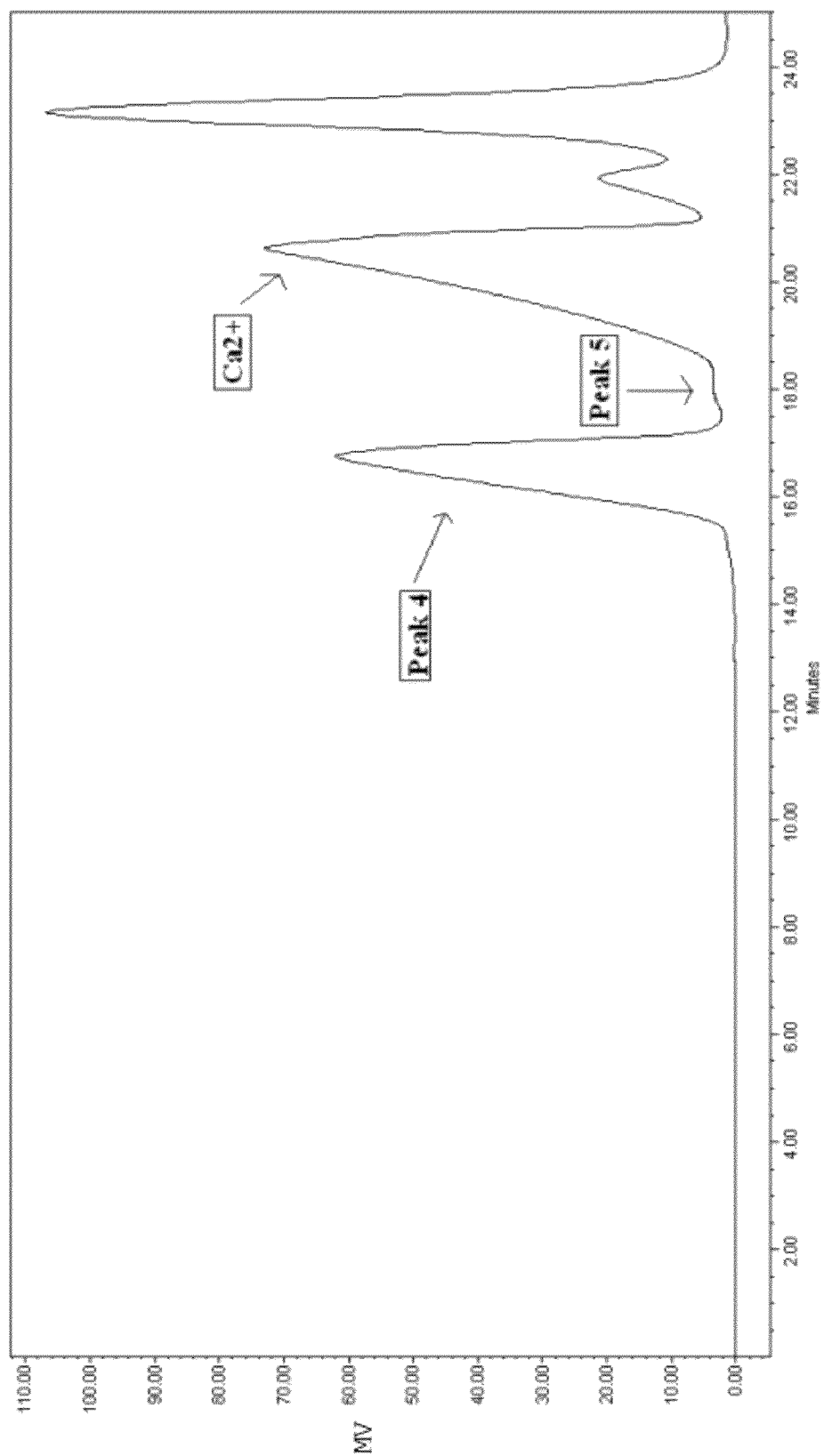
FIG. 4 illustrates an SEC chromatogram having exclusive peaks 4 and 5 for an inventive product, Example 3, of the present invention.
Figure 5:
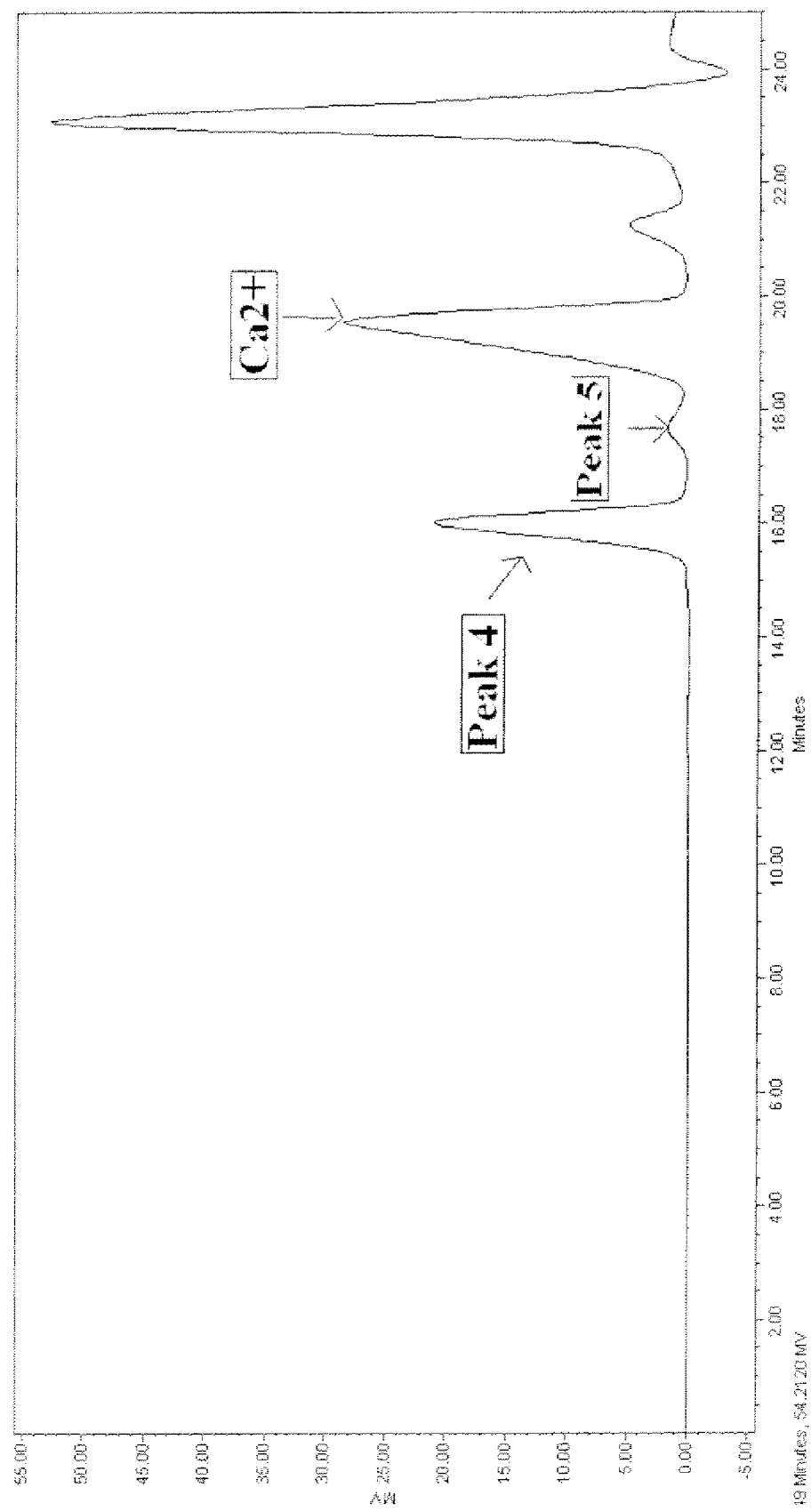
FIG. 5 illustrates an SEC chromatogram having exclusive peaks 4 and 5 for an inventive product, Example 4, of the present invention.
Figure 6:
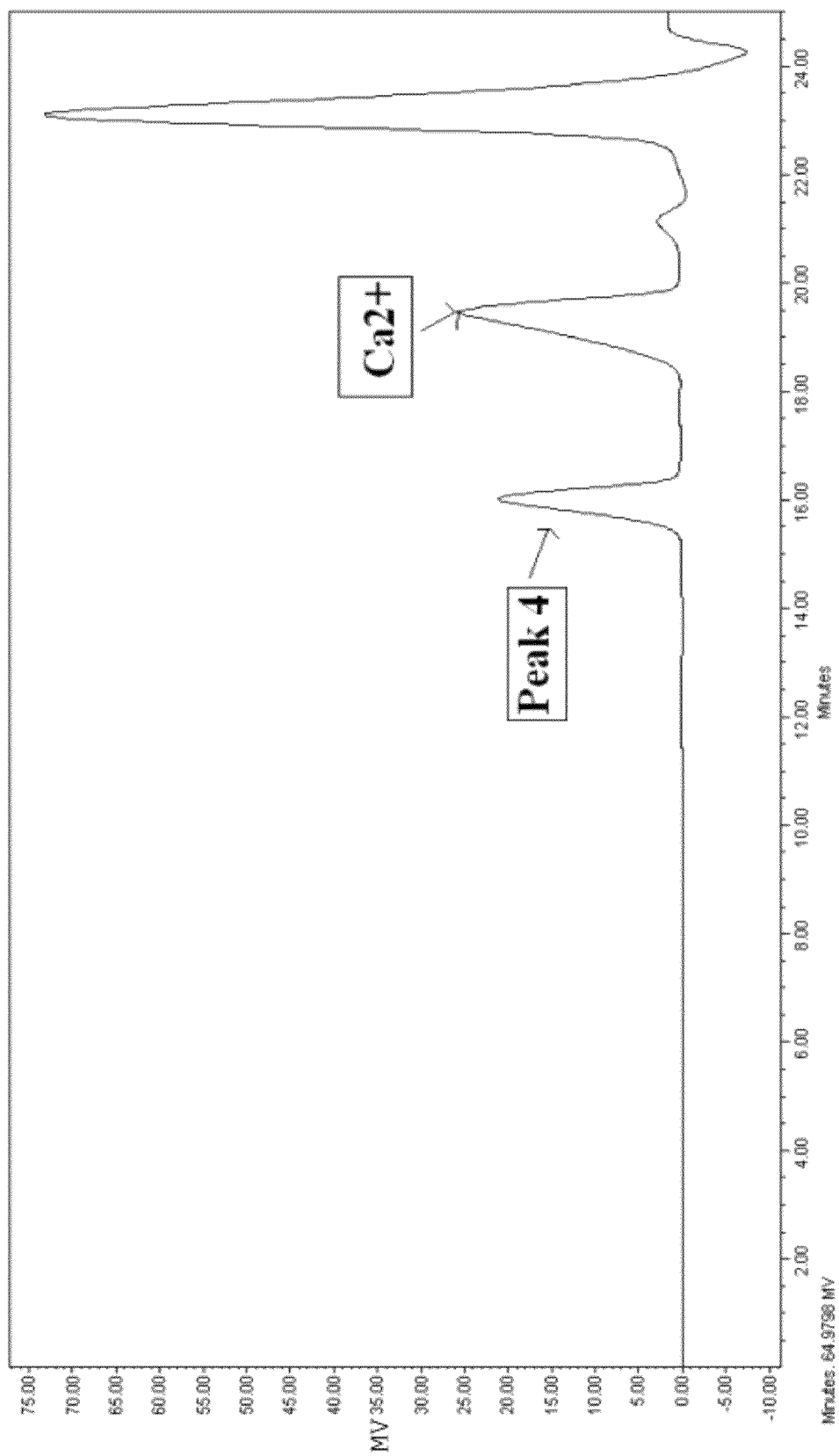
FIG. 6 illustrates an SEC chromatogram having exclusive peak 4 for an inventive product, Example 5, of the present invention.
Figure 7:
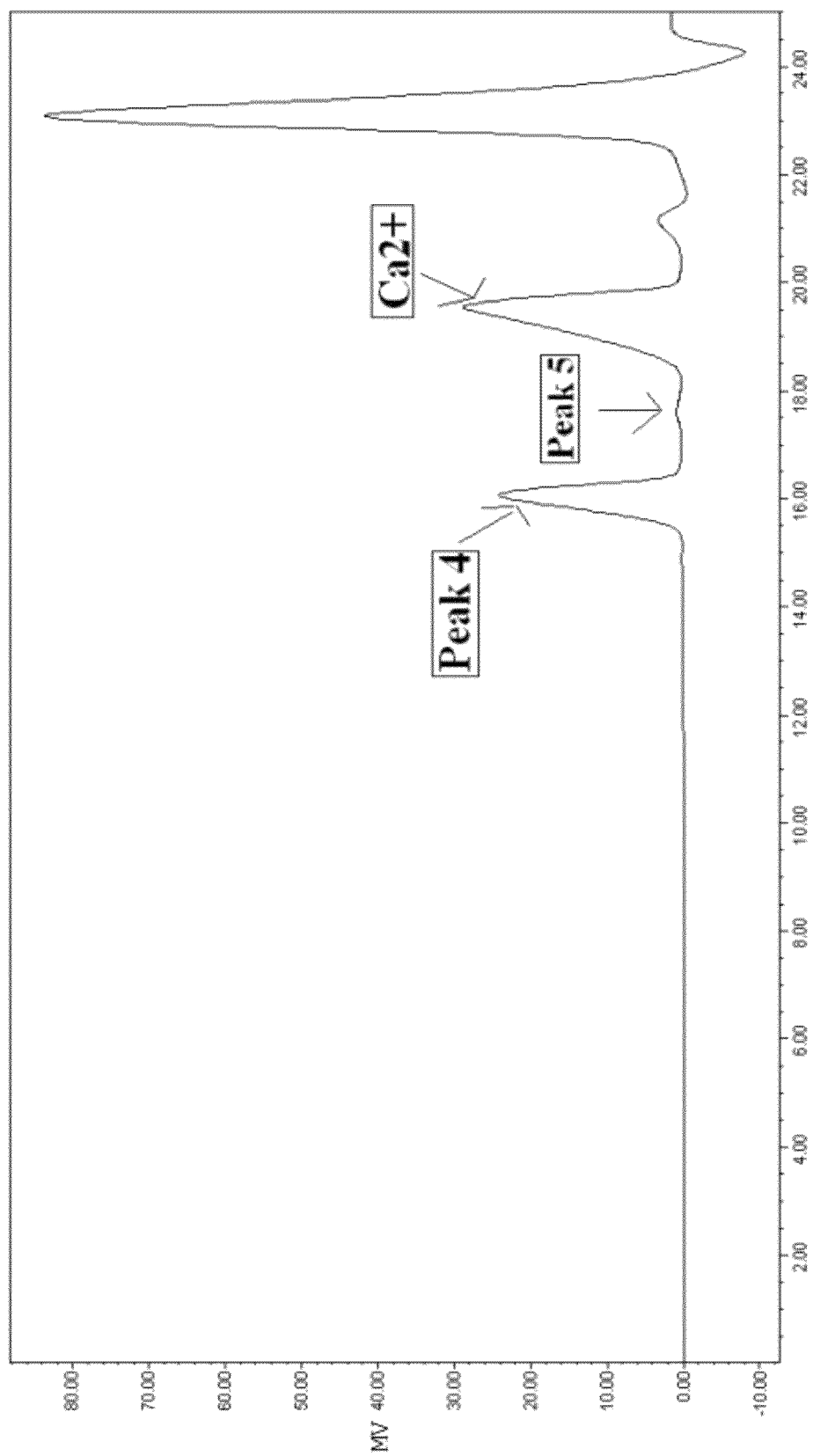
FIG. 7 illustrates an SEC chromatogram having exclusive peaks 4 and 5 for an inventive product, Example 6, of the present invention.

A small portion of the solution from Example 2 is taken to determine the effects of Zr on the peak distribution. $ZrOCl_2.8H_2O$ is added to achieve a molar ratio of 8:1, Al:Zr. The pH after adding Zr reduces to 3.7. As shown in FIG. 4, the SEC chromatogram of this zirconium, aluminum solution shows notable features. Firstly, the SEC-Peak 4 remains the predominate peak, and the SEC-Peak 5 intensity increased to 1%—as expected by the reduced pH. Secondly, the SEC chromatogram does not show an peaks with retention time of 12.5 minute indicating the absence of undesirable Zr polymer species. The absence of this C-Peak indicates that the pure SEC-Peak 4 solution of Example 2 did not promote the aggregation of Zr into larger, less efficacious species. Also substantially SEC-Peak 3 species is observed at a retention time of approximately 15.5 minutes.

Example 4

A 0.5M $AlCl_3.6H_2O$ (25 mmol) is buffered with 31.25 mmol glycine, held at 95° C., and stirred vigorously. To this buffered solution, a 1.0 N Ca $(OH)_2$ (31.25 mmol) is added dropwise over a 1 hour period. A ratio of OH:Al of 2.5 is employed in an attempt to increase the final pH and to reduce SEC-Peak 5 species. The pit after the reaction is 4.52. The SEC chromatogram shown in FIG. 5 exhibits primarily SEC-Peak 4 and a smaller SEC-Peak 5 (520). Substantially no SEC-Peak 3 species is observed at a retention time of approximately 15.5 minutes.

Example 5

A 0.5M $AlCl_3.6H_2O$ (25 mmol) is buffered with 62.5 mmol glycine, held at 9.5° C., and stirred vigorously. To this buffered solution a 1.0 N CA $(OH)_2$ (31.25 mmol) is added dropwise over a 1 hour period. A ratio of OH:Al of 2.5 is employed in an attempt to increase the final pH and to reduce the SEC-Peak 5 species. The pH after the reaction is 4.52. The SEC chromatogram shown in FIG. 6 exhibits exclusively SEC-Peak 4 and no SEC-Peak 5. Substantially no SEC-Peak 3 species is observed at a retention time of approximately 15.5 minutes.

Example 6

A small portion of the solution from Example 5 is taken to determine the effects of Zr on the peak distribution. $ZrOCl_2.8H_2O$ is added to achieve an Al:Zr molar ratio of 8:1. The pH after adding Zr reduces to 3.3. The SEC chromatogram shown in FIG. 7 exhibits primarily SEC-Peak 4 and substantially no SEC-Peak 5 (720). This data indicates that the pure SEC-Peak 4 solution of Example 5 does not promote the aggregation of Zr into larger, less efficacious species. Also substantially no SEC-Peak 3 species is observed at a retention time of approximately 15.5 minutes.

Example 7

Process:
1. Aluminum chloride hexandyrate (3.1055 kg) and anhydrous glycine (1.1863 kg) were combined in a 316 stainless steel, 25 gallon batch vessel provided with two level hydrofoil blade agitation using medium (60-80 rpm) agitation. Distilled water (19.8192 kg) was added to the mixture and the solution was heated to 85° C. with vigorous (100-125 rpm) agitation. Temperature control was used to maintain effective temperature rate increase and target level during the trial. The heating source was a steam jacket provided with 3 bar/42 psig steam throughout the trial.
2. in a separate reaction vessel, calcium hydroxide (1.1725 kg) dissolved in 4.7165 kg of distilled water,
3. When the aluminum chloride hexandyrate/glycine solution reached 85° C., the calcium hydroxide solution was added over a 1 hour 30 minute period. The reaction vessel was vigorously agitated throughout the addition and care was taken to ensure that the calcium hydroxide residue did not form at the top of the vessel.
4. After the addition of calcium hydroxide, the solution was held at 85° C. under vigorous agitation for an additional three hours. The reaction yielded 30.18 kg (100.4%) of ACH.

Figure 8:
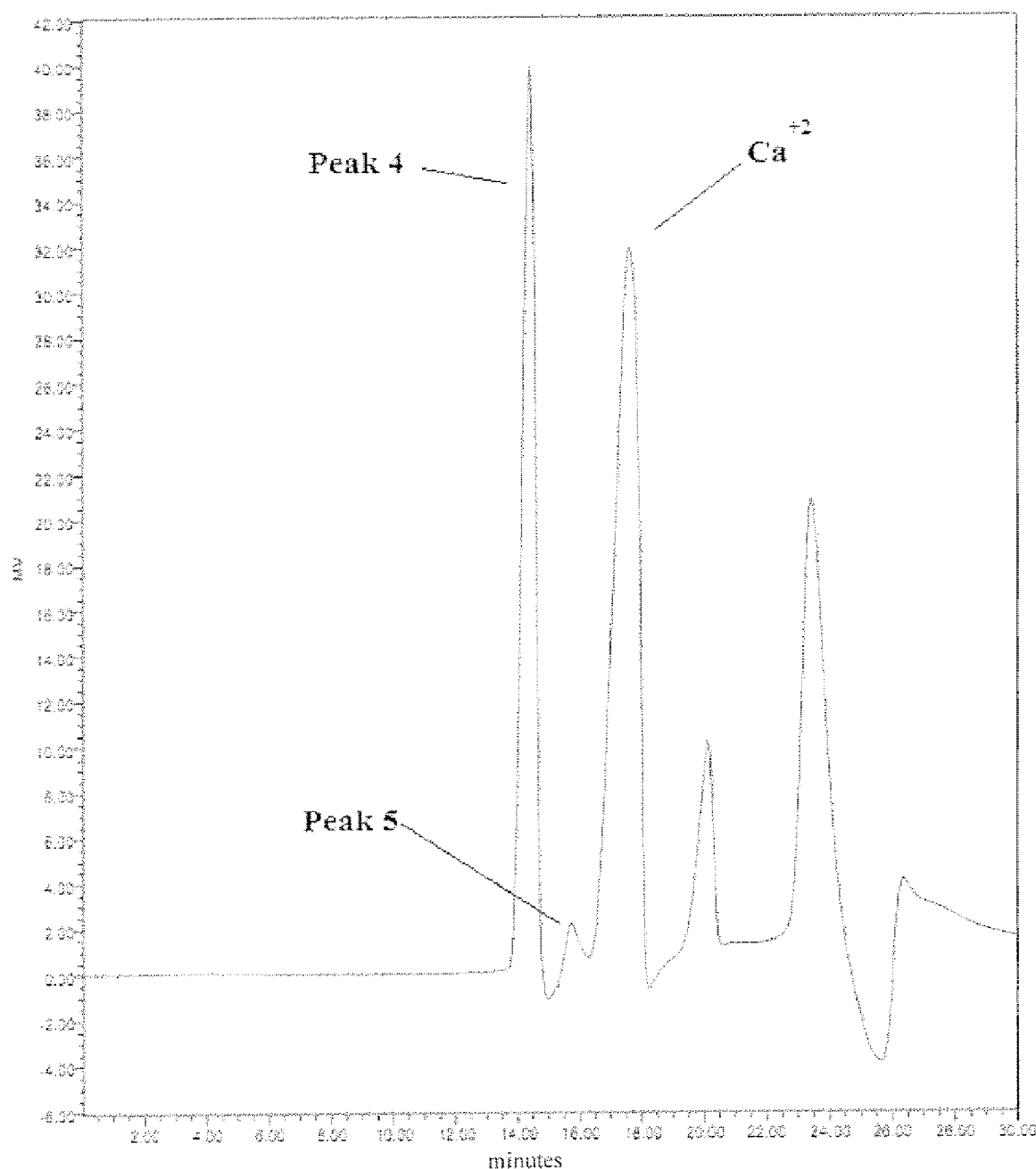
FIG. 8 illustrates an SEC chromatogram of an inventive product from an ACH batch scale-up, Example 7, of the present invention.

Analysis:

SEC analysis showed that the scaled-up synthesis of ACH was successful in replicating laboratory results: the resultant active solution was void of Peaks 1-3 and contained a very small Peak 5. FIG. 8 shows the SEC profile of the product from the ACH batch scale-up in which Peak 4 elutes at 14.5 minutes in both SEC profiles. Visual analysis clearly indicates that Peaks 1-3 are absent from the ACH solution. There is also a strong Peak 4 and a minimal Peak 5. The results of Peak distribution are summarized in Table 2 below.

TABLE 1

Comparison of the Examples

| Example | Ratio OH:Al | pH | Comparable ACH Solution | Relative Peak Distribution after Reaction (%) | | | | Peak 4/Peak 3 |
|---|---|---|---|---|---|---|---|---|
| | | | | Peak 2 | Peak 3 | Peak 4 | Peak 5 | |
| Summit ™ Z576 | | | | 3.1 | 34.1 | 40 | 22.6 | 1.2 |
| Reach ™ 103 | n/a | | 10% ACH | | 63 | 34 | 3 | 0.54 |
| Reach ™ 301 | n/a | | 10% ACH | 7 | 65 | 12 | 16 | 0.18 |
| Comparative | 2.2 | 2.36 | 21% ACH | 0 | 42 | 42 | 16 | 1.0 |
| Example 1 | 2.2 | 2.56 | 21% ACH | 0 | 0 | 75 | 25 | ∞ |
| Example 2 | 2.5 | 4.8 | 22% ACH | 0 | 0 | 100 | 0 | ∞ |
| Example 3 | 2.5 | 3.7 | 22% ACH | 0 | 0 | 99 | 1 | ∞ |
| Example 4 | 2.5 | 4.5 | 4% ACH | 0 | 0 | 93 | 7 | ∞ |
| Example 5 | 2.5 | 4.52 | 4% ACH | 0 | 0 | 100 | 0 | ∞ |
| Example 6 | | 3.32 | 4% ACH | 0 | 0 | 98 | 2 | ∞ |

TABLE 2

Comparison of Peak Distribution of the Scaled-up Batch (ACH) vs. an Activated ACH (Reach ™ 103)

| Solution | Relative Peak Distribution after Reaction (%) | | | Peak 4/Peak 3 | pH |
|---|---|---|---|---|---|
| | Peak 3 | Peak 4 | Peak 5 | | |

Large Scale Production of Antiperspirant Active Compositions

| | | | | | |
|---|---|---|---|---|---|
| Reach ™ 103 | 61.00 | 35.7 | 3.3 | 0.585 | 4.07 |
| Example 7 | 0 | 96.74 | 3.26 | ∞ | 3.89 |

CONCLUSION

The result of scaled-up batching in the pilot shows its uniform aluminum species under Peak 4 can be obtained in contrast to un-removable larger species in current activated ACH (Reach™ 103). The process of the present invention can be successfully adopted into any large facility antiperspirant manufacturers.

Figure 9:
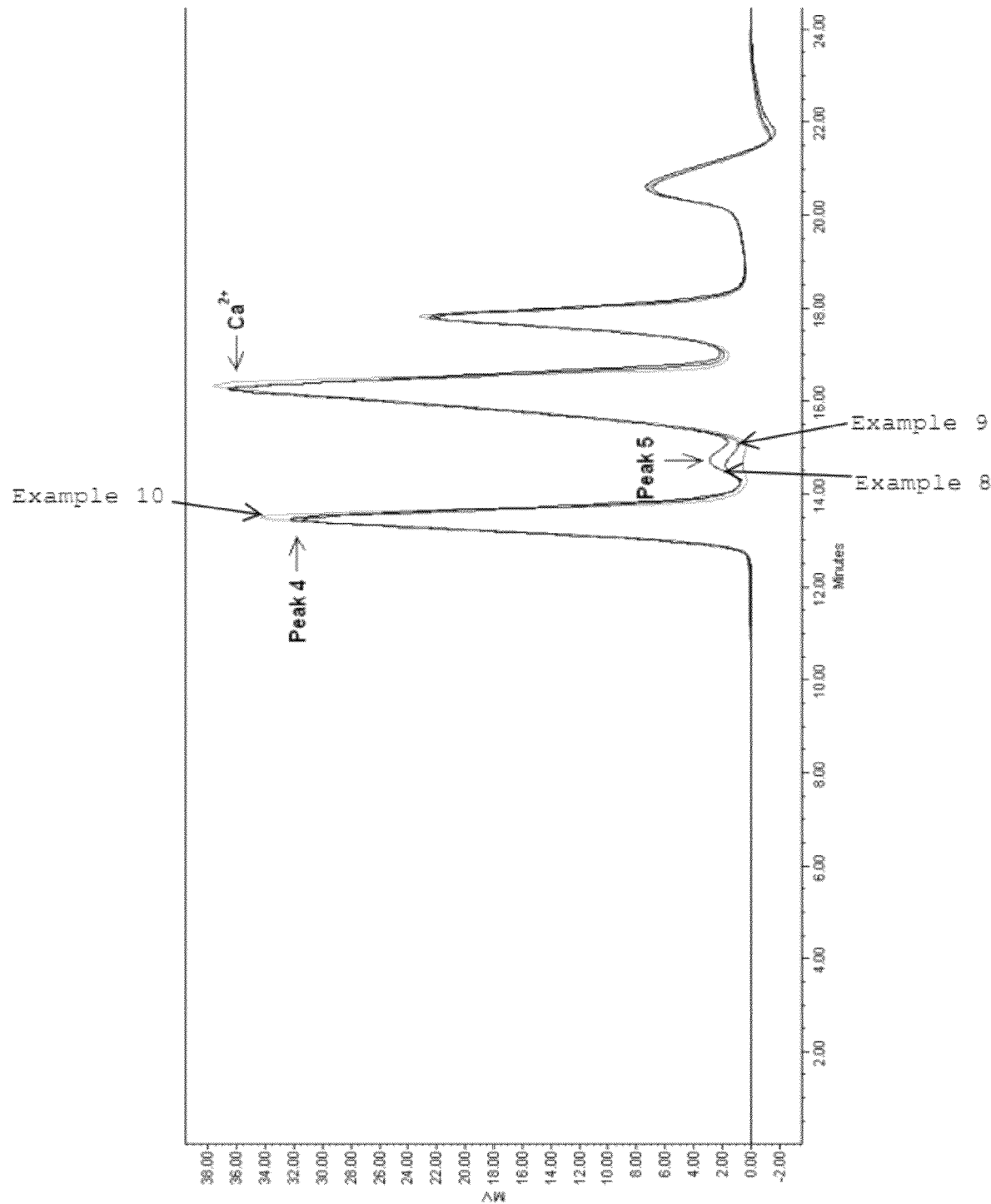
FIG. 9 illustrates an SEC chromatogram for inventive products. Examples 8-10, of the present invention produced within an optimal reaction temperature range.

Optimal Reaction Parameters for Manufacturing Process
Optimal Reaction Temperature The reactions for the following Examples 8-10 were all performed with a $Ca(OH)_2$:glycine molar of 1:1 and a OH:Al molar ratio of 2.46:1. In all three reactions, a 0.65 M $AlCl_3.6H_2O$ (19 mmol) aqueous solution as buffered with 23 mmol glycine and heated to 90° C. with stirring. A $Ca(OH)_2$ suspension was added drop-wise by hand to the aqueous aluminum chloride salt solution over 1 hour and 40 minutes, with a total reaction time of 3.5 to 4 hours. The SEC chromatogram in FIG. 9 illustrates large Peak 4 with negligible Peak 3 for Examples 8-10. There is little to no increase in Peak 3 formation upon lowering the reaction temperature from 90° C. to 75° C. There is only a small increase of 3.9%-6.9% for Peak 5 upon lowering the reaction temperatures. A small Peak 5 will add to the long term stability and efficacy of the active product. Therefore, the optimal reaction temperature is between 75° C. and 90° C. According to the SEC peak areas in FIG. 9, the solutions of Examples 8-10 are approximately comparable to a ~5% ACH solution.

TABLE 3

Comparison of the Examples (75° C. vs. 90° C.)

| Solution | Basic Source | Relative Peak Distribution after Reaction (%) | | | Comparable ACH (%) | Temperature (° C.) |
|---|---|---|---|---|---|---|
| | | Peak 3 | Peak 4 | Peak 5 | | |
| Example 8 | $Ca(OH)_2$ | 0 | 92.0 | 8.0 | 5.6 | 75 |
| Example 9 | $Ca(OH)_2$ | 0.2 | 94.8 | 5.0 | 5.2 | 75 |
| Example 10 | $Ca(OH)_2$ | 0 | 98.9 | 1.1 | 4.9 | 90 |

Optimal Reaction Time For Synthesis of ACH

Figure 10:
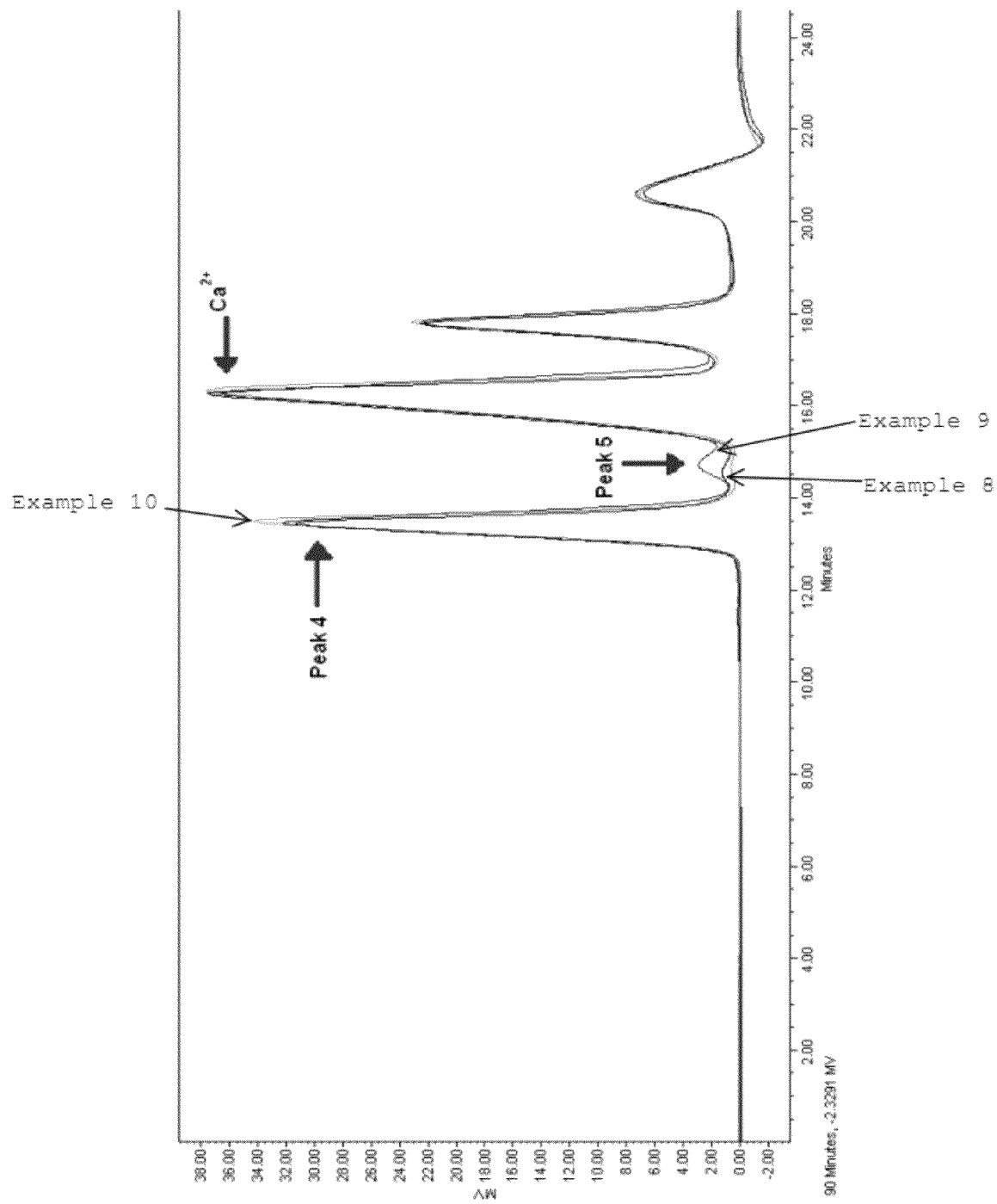
FIG. 10 illustrates an SEC chromatogram for inventive products, Examples 8, 10, and 11, of the present invention produced within an optimal reaction time range.

The reactions for the following Examples 8, 10, and 11, were all performed with a $Ca(OH)_2$:glycine molar ratio of 1:1 and a OH:Al molar ratio of 2.46:1. The total reaction time for all three examples was 3-4 hours. The SEC chromatogram in FIG. 10 shows only a 0.2% increase in Peak 3 upon lowering the reaction time to 3 hours at 70° C. According to the SEC peak area, the solutions for Examples 8, 10, and 11 are comparable to a ~5% ACM solution. FIG. 10 further shows exclusively Peaks 4 and 5 in reactions performed at 75° C. and 90° C. for 4 hours (respectively, Examples 8 and 10).

Figure 11:
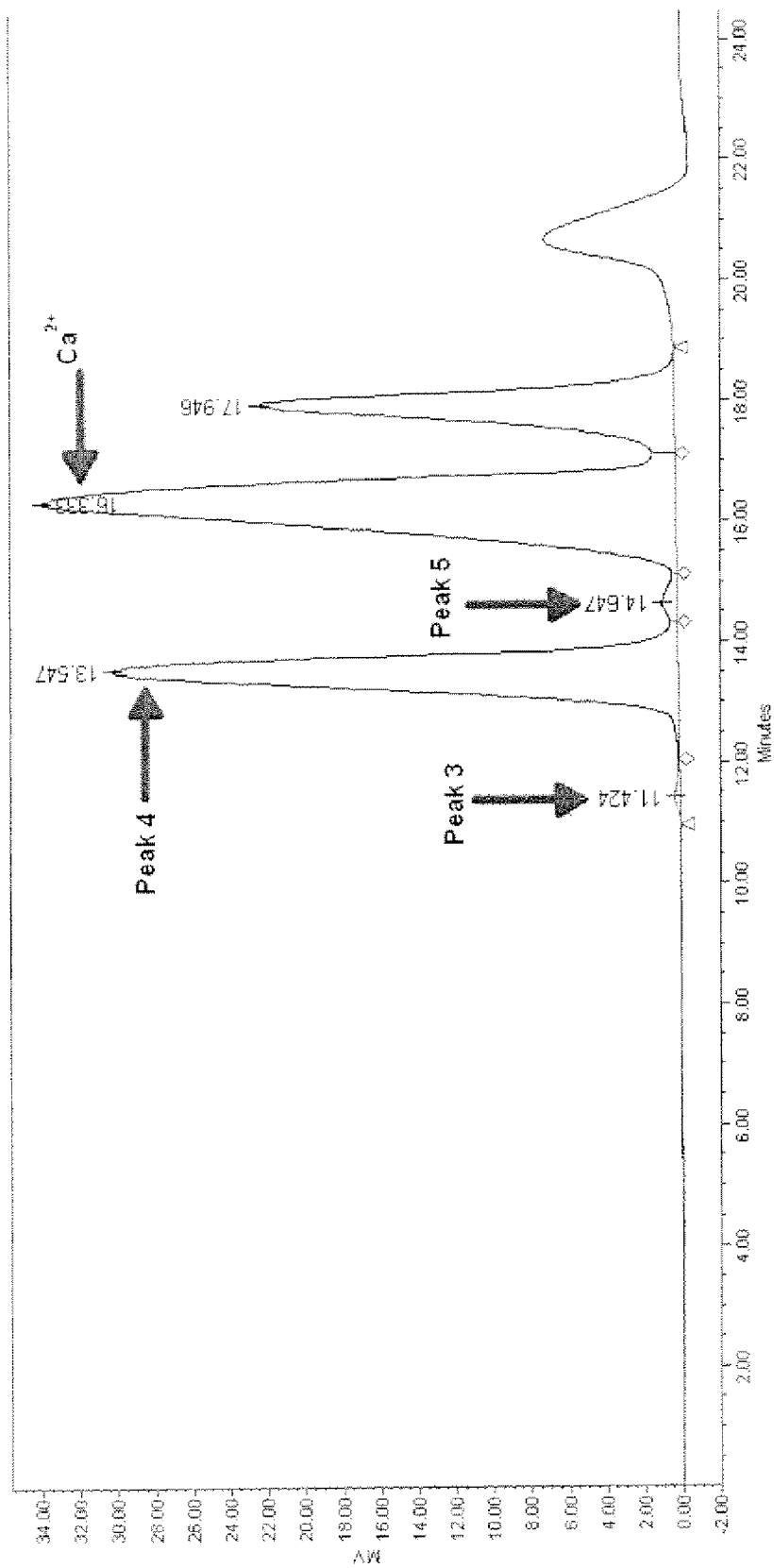
FIG. 11 illustrates an SEC chromatogram for an inventive product, Example 1.2, of the present invention produced within an optimal reaction time range.

The reaction for Example 12 was performed with a $Ca(OH)_2$:glycine molar ratio of 1.25:1 and a OH:Al molar ratio of 2.46:1. The SEC chromatogram in FIG. 11 shows favorable results when the reaction was performed using optimal parameters and reacted at 75° C. for 3 hours and 30 minutes. FIG. 11 also shows an increase in Peak 3 of 0.8% and an increase of 2.4% for Peak 5 upon lowering the reaction time to 3 hours and 30 minutes at 75° C. According to the SEC peak areas in FIG. 11, the solution of Example 12 is approximately comparable to a ~5% ACH solution. Therefore, the optimal reaction time is between 3 and 4 hours.

TABLE 4

Comparison of Example Reaction Times

| Solution | Basic Source | Relative Peak Distribution after Reaction (%) | | | Comparable ACH (%) | Temperature (° C.) | Reaction Time (hrs) |
|---|---|---|---|---|---|---|---|
| | | Peak 3 | Peak 4 | Peak 5 | | | |
| Example 8 | $Ca(OH)_2$ | 0 | 92.0 | 8.0 | 5.6 | 75 | 4 |
| Example 10 | $Ca(OH)_2$ | 0 | 98.9 | 1.1 | 4.9 | 90 | 4 |
| Example 11 | $Ca(OH)_2$ | 0.2 | 96.8 | 3.0 | 4.7 | 70 | 3 |
| Example 12 | $Ca(OH)_2$ | 0.8 | 96.7 | 2.5 | 5.2 | 75 | 3.5 |

Optimal $Ca(OH)_2$:Glycine Molar Ratio

Figure 12:
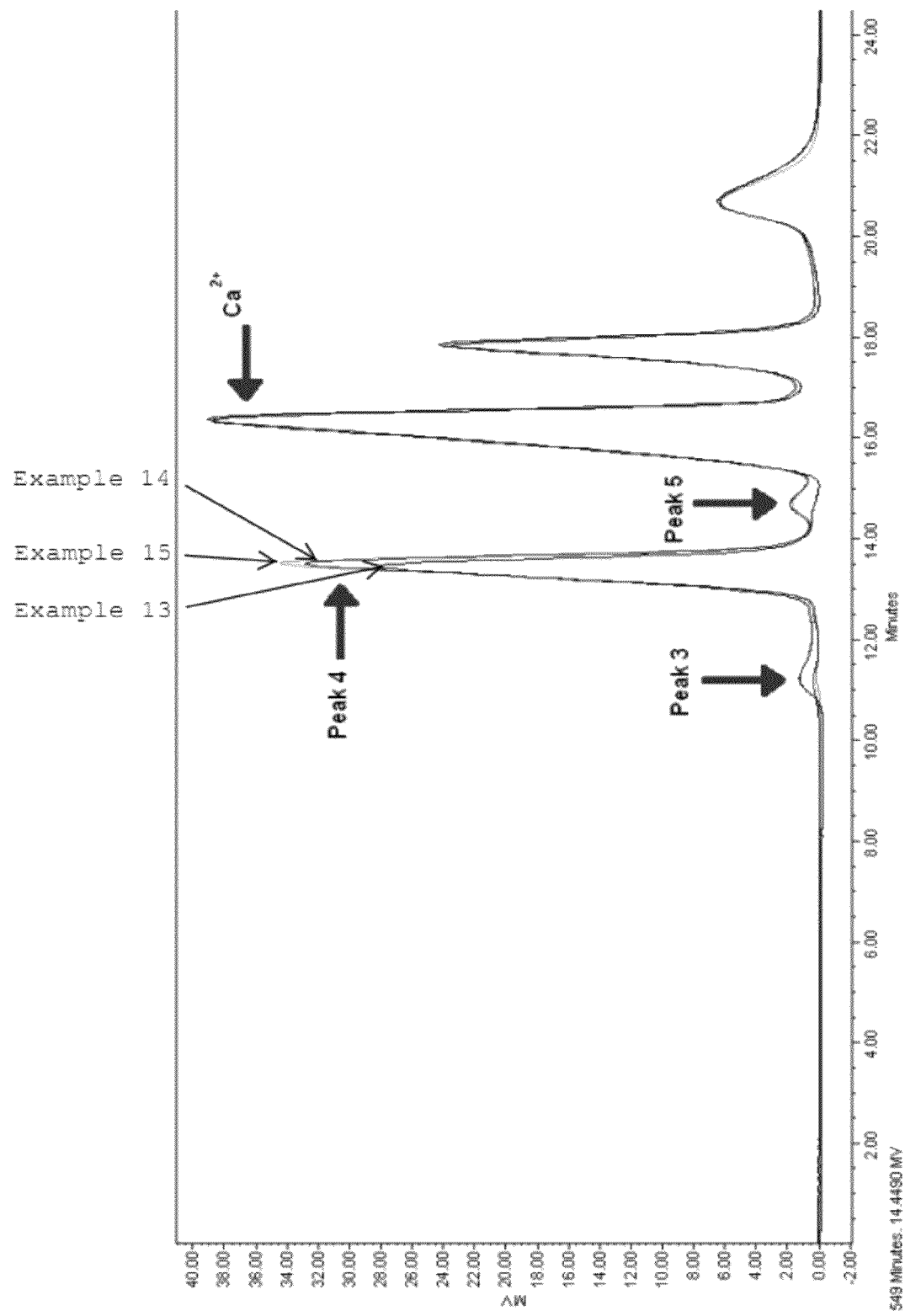
FIG. 12 illustrates an SEC chromatogram for inventive products, Examples 13-15, of the present invention produced within an optimal Ca(OH)$_2$:glycine molar ratio range.

The reactions for the following Examples 13-15 were all performed using an OH:Al molar ration of 2.46:1 and were reacted for 2-4 hours. For Examples 13-15, a 0.235 M $AlCl_3.6H_2O$ (47 mmol) aqueous solution was buffered with 23 mmol glycine and heated to 90° C. with stirring. FIG. 12 and Table 5 illustrate that the closer the $Ca(OH)_2$:glycine molar ratio is to a 1:1 value, the smaller the relative distribution percentage of Peak 3. A $Ca(OH)_2$:glycine molar ratio of 2.5:1 (Example 13) produced an increase in Peak 3 by 7.8% compared to the standard reaction (Example 10). A $Ca(OH)_2$:glycine molar ratio of 2:1 (Example 14) was used, there was a 1.4% increase in Peak 3. When the $Ca(OH)_2$:glycine molar ratio was lowered to 1.25:1 (Example 15), there was only a 0.4% increase in Peak 3. Using $Ca(OH)_2$:glycine molar ratio of 1.25:1 produces a high Peak 4/Peak 3 ratio. Example 12 illustrates that an increase of only 0.8% in Peak 3 when using a $Ca(OH)_2$:glycine molar ratio 1.25:1 at 75° C. Following the optimal reaction parameters, there was only a 0.4% increase in Peak 3 compared to Example 15 done at 90° C. Therefore, the optimal $Ca(OH)_2$:glycine molar ratio is between 25:1 and 1:1.

TABLE 5

Comparison of Example Ca(OH)$_2$:Glycine Molar Ratios

| Solution | Basic Source | Relative Peak Distribution after Reaction (%) | | | Comparable ACH (%) | Temperature (° C.) | Ca(OH)$_2$:glycine |
|---|---|---|---|---|---|---|---|
| | | Peak 3 | Peak 4 | Peak 5 | | | |
| Example 12 | Ca(OH)$_2$ | 0.8 | 96.7 | 2.5 | 5.2 | 75 | 1.25:1 |
| Example 13 | Ca(OH)$_2$ | 7.8 | 92.2 | 0 | 4.7 | 90 | 2.5:1 |
| Example 14 | Ca(OH)$_2$ | 1.4 | 93.0 | 5.6 | 5.0 | 90 | 2:1 |
| Example 15 | Ca(OH)$_2$ | 0.4 | 94.8 | 4.8 | 5.1 | 90 | 1.25:1 |

Optimal Revolutions Per Minute (RPM)

Figure 13:
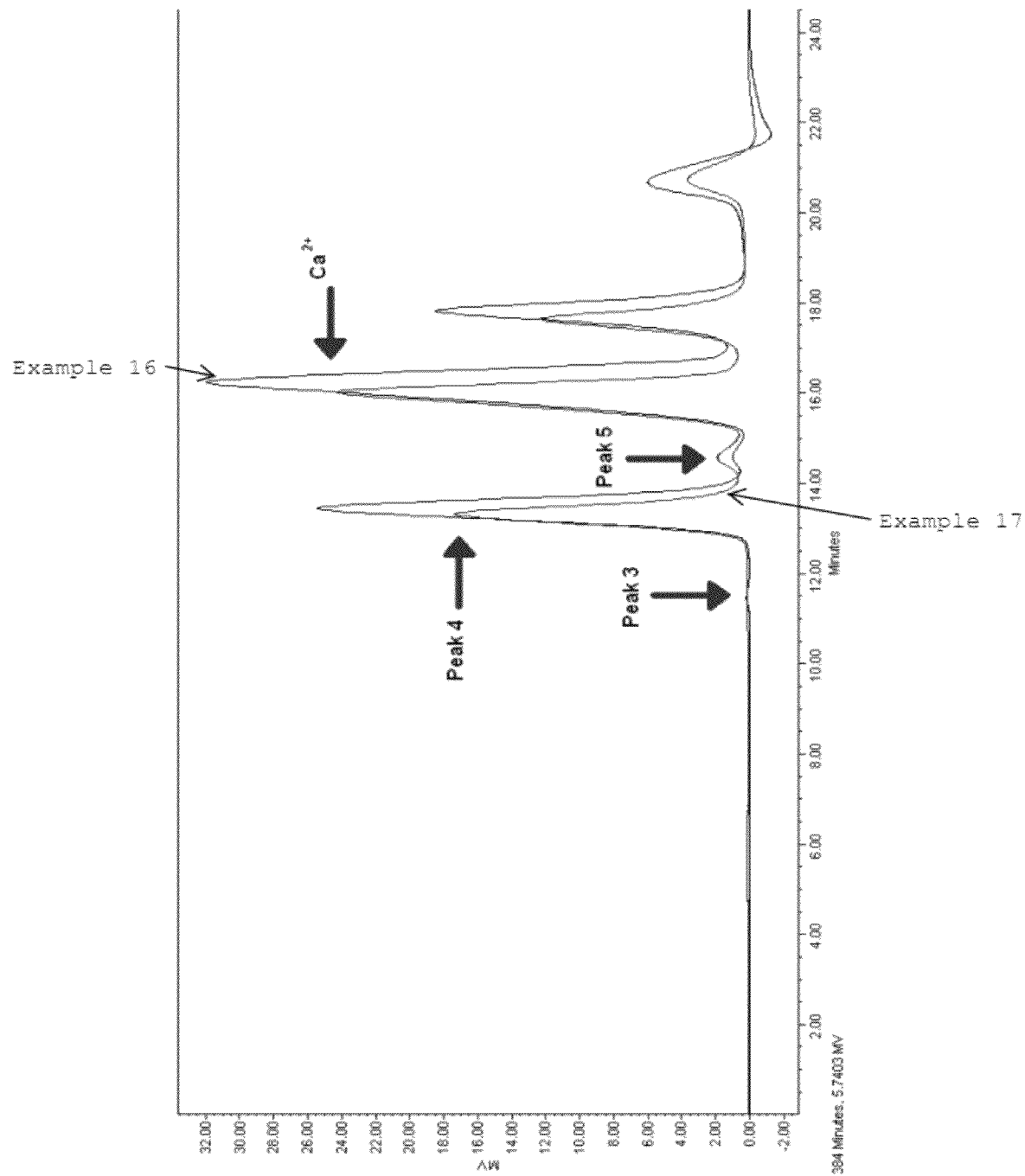
FIG. 13 illustrates an SEC chromatogram for inventive products, Examples 16 and 17, of the present invention produced at different revolutions per minute.
Figure 14:
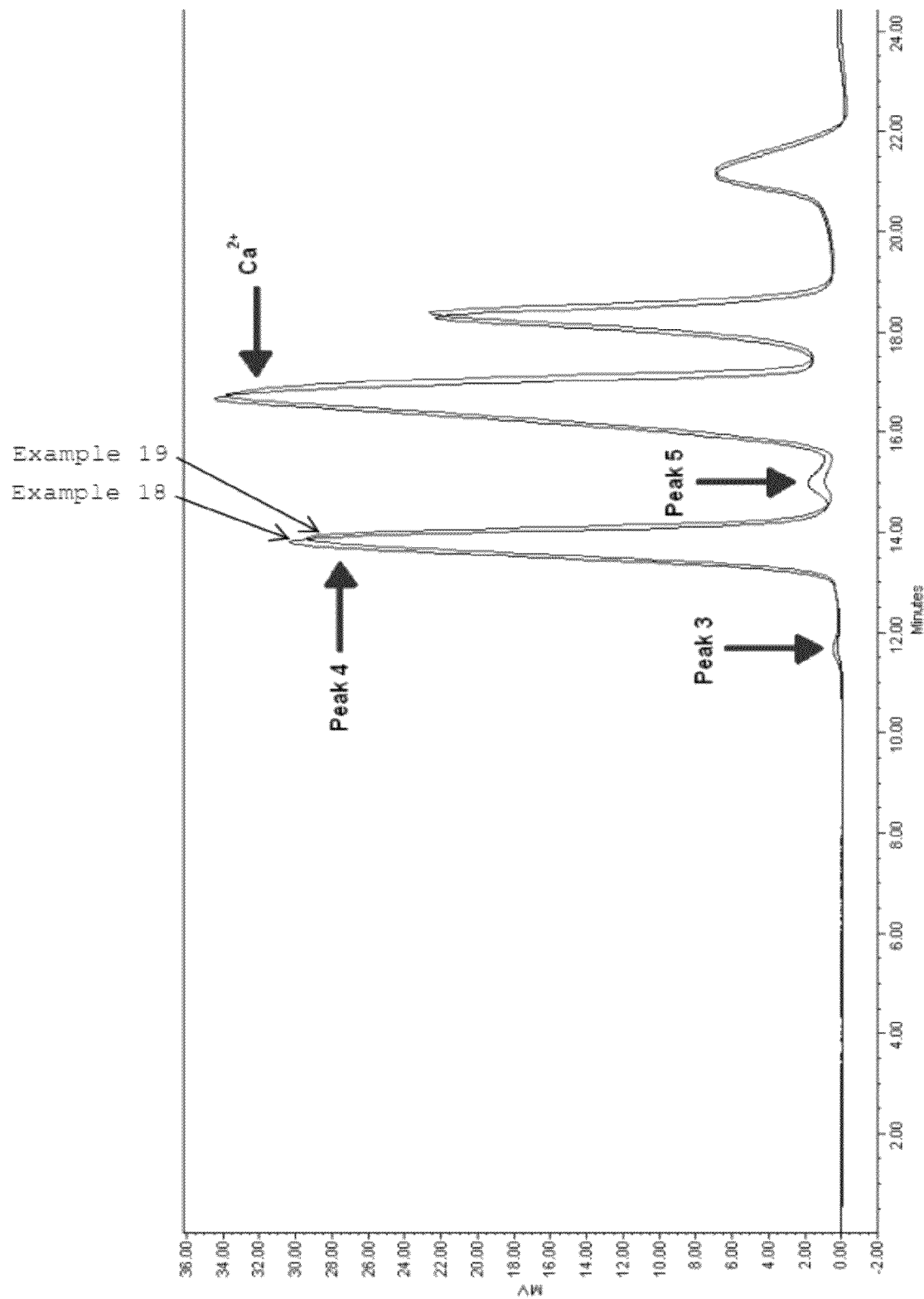
FIG. 14 illustrates an SEC chromatogram for inventive products, Examples 18 and 19, of the present invention produced within an optimal revolutions per minute range.

The ACH synthesis of Example 10 at 90° C. over 4 hours used a magnetic stir bar for stirring. This method does not provide for a way to specifically control the revolutions per minute (rpm) of the stirring and results in a product with a great deal of unreacted calcium hydroxide present. The first two reactions were performed at 200 rpm and 450 rpm, without covering the top of the reaction flask. This resulted in water loss and turned the solution into a gel which made analysis impossible. Thus, it is clear that water loss must be minimized while stirring the reaction to ensure favorable results. FIG. 13 illustrates the success of reducing water loss and stirring the mixture at a high rpm. Examples 16 and 17 below were performed using an Erlenmeyer flask fitted with a rubber stopper to help minimize water loss and at 750 rpm and 250 rpm, respectively. Examples 18 and 19 were performed at 600 rpm and 400 rpm, respectively. It is clear that a higher rpm produces a more favorable product by reducing the formation of Peak 3. FIG. 14 illustrates that running the reaction at 500 rpm produced a 0.8% increase in Peak 3 and a slight increase in Peak 5. Therefore, the optimal revolutions per minute are between 500 and 600 rpm for the method of this example.

Optimal Method for the Addition of Ca(OH)$_2$

Figure 15:
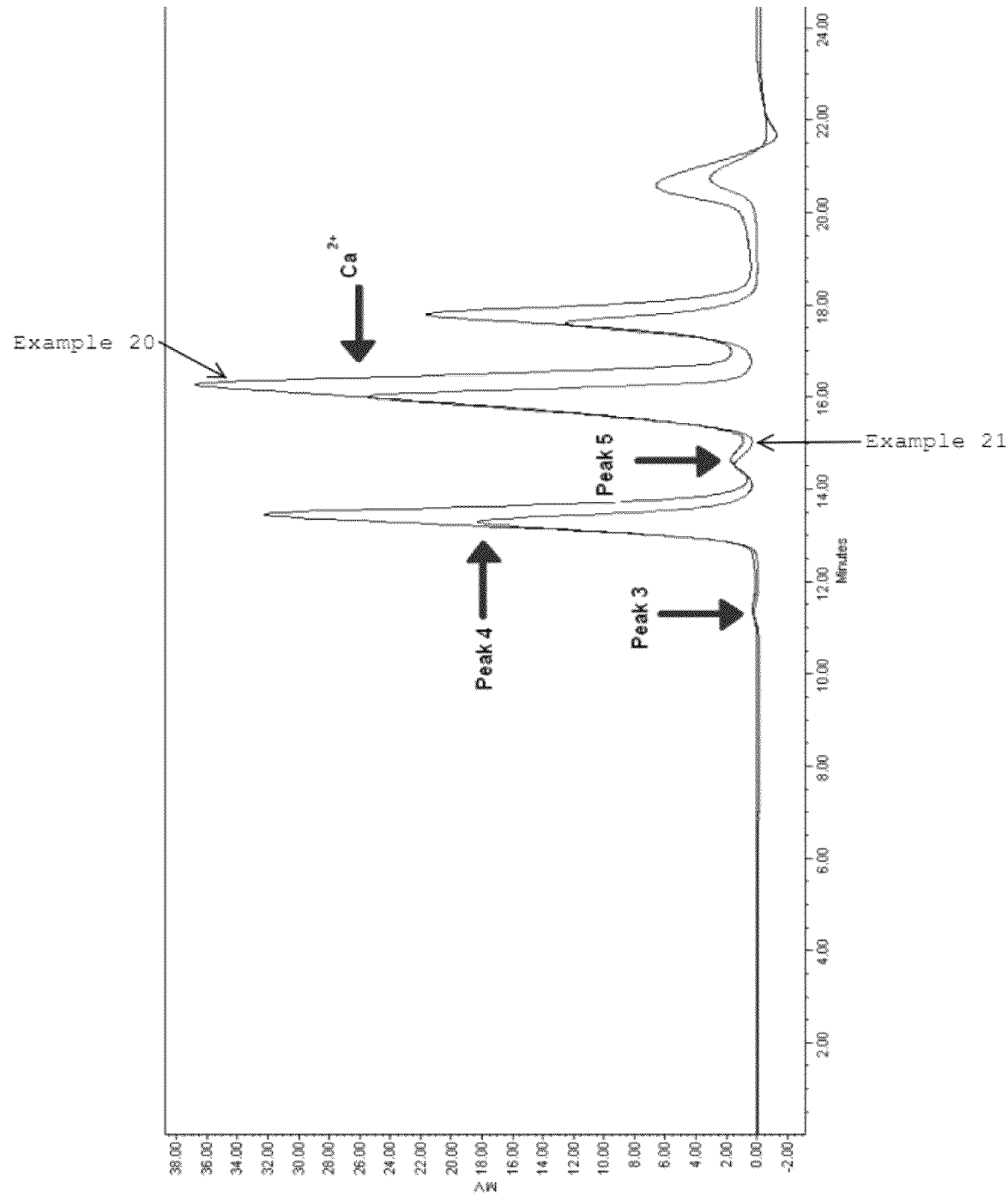
FIG. 15 illustrates an SEC chromatogram for inventive products, Examples 20 and 21, of the present invention produced by different methods of adding $Ca(OH)_2$.

Simultaneous addition of aluminum chloride, glycine, and calcium hydroxide then mixing and heating yields unfavorable results: 25.5% Peak 3 and 16.7 Peak 5 which are poor for the formation of a pure Peak 4 complex. Also studied was the addition of a calcium hydroxide power to an aqueous aluminum chloride salt solution once the reaction was at 90° C. This produced increases in Peak 3 by 4.3% to 7.3%, and increases in Peak 5 by 13.3% to 17%. FIG. 15 and Table 7 below illustrate the benefit of using a calcium hydroxide solution compared to a powder. Using a calcium hydroxide solution (Example 20) produced a 1% smaller Peak 3 and a 3.9% smaller Peak 5 compared to using a calcium hydroxide powder (Example 21). The calcium hydroxide in Examples 20 and 21 were added to the aluminum chloride salt solution 4 times over 1.5 hours. Further, the addition of a calcium hydroxide suspension initially occurred drop-wise by hand over 1 hour and 45 minutes. However, Example 10 and FIG. 11 illustrates favorable results obtained from adding a calcium hydroxide solution 5 times over 1 hour and 45 minutes, following all other optimal reaction conditions. Therefore the optimal way to add Ca(OH)$_2$ is in solution form over several additions.

TABLE 6

Comparison of Example Revolutions Per Minute (RPM)

| Solution | Basic Source | Relative Peak Distribution after Reaction (%) | | | Comparable ACH (%) | RPM |
|---|---|---|---|---|---|---|
| | | Peak 3 | Peak 4 | Peak 5 | | |
| Example 16 | Ca(OH)$_2$ | 0.2 | 89.9 | 9.9 | 2.7 | 750 |
| Example 17 | Ca(OH)$_2$ | 0.6 | 96.2 | 3.2 | 4.0 | 250 |
| Example 18 | Ca(OH)$_2$ | 0.6 | 94.3 | 5.1 | 5.3 | 600 |
| Example 19 | Ca(OH)$_2$ | 1.2 | 96.6 | 2.2 | 5.2 | 400 |

TABLE 7

Comparison of Ca(OH)$_2$ solution vs. Ca(OH)$_2$ powder

| Solution | Basic Source | Relative Peak Distribution after Reaction (%) | | | Comparable ACH (%) | No. of Additions |
|---|---|---|---|---|---|---|
| | | Peak 3 | Peak 4 | Peak 5 | | |
| Example 20 | Ca(OH)$_2$ solution | 0.6 | 94.7 | 4.7 | 4.9 | 4 additions over 1.5 hours |
| Example 21 | Ca(OH)$_2$ powder | 1.6 | 89.8 | 8.6 | 2.7 | 4 additions over 1.5 hours |

What is claimed is:

1. An antiperspirant active composition comprising an aluminum chlorohydrate salt having an aluminum to chloride molar ratio of about 0.3:1 to about 3:1, exhibiting a SEC chromatogram having a SEC Peak 4 to Peak 3 intensity ratio of at least 16 and a Peak 4 intensity greater than a Peak 5 intensity in aqueous solution.

2. The antiperspirant active of claim 1, wherein the aluminum chlorohydrate salt further comprises zirconium to form an aluminum-zirconium salt.

3. The antiperspirant active of claim 1, wherein the aluminum chlorohydrate salt is buffer free and has an OH to Al ratio of about 2:1 to about 2.6:1.

4. The antiperspirant active of claim 1 further comprising a buffer, wherein a molar ratio of buffer to aluminum is about 0.1:1 to about 3:1.

5. The antiperspirant active of claim 4, wherein the buffer is at least one buffer chosen from an amino acid, glycine, and betaine.

6. The antiperspirant active of claim 2, wherein a molar ratio of aluminum to zirconium is about 5:1 to about 10:1.

7. The antiperspirant active composition of claim 1, wherein the composition has a SEC Peak 4 area of 95 to 100% of a total area of Peaks 1, 2, 3, 4, 5, and 6 in the SEC chromatogram.

8. The antiperspirant active composition of claim 1, wherein the composition has a SEC Peak 3 area of less than about 5% of a total area of Peaks 1, 2, 3, 4, 5, and 6 in the SEC chromatogram.

9. The antiperspirant active composition of claim 1, wherein the composition has no SEC Peak 3 area in the SEC chromatogram.

10. The antiperspirant active composition of claim 1, wherein the composition has a SEC Peak 5 area of less than 30% of a total area of Peaks 1, 2, 3, 4, 5, and 6 in the SEC chromatogram.

11. The antiperspirant active composition of claim 1, wherein the composition has no SEC Peak 5 area in the SEC chromatogram.

12. The antiperspirant active composition of claim 1, wherein the composition has a SEC Peak 1 area of less than 10% and a SEC Peak 2 area of less than 10% of a total area of Peaks 1, 2, 3, 4, 5, and 6 in the SEC chromatogram.

13. The antiperspirant active composition of claim 1, wherein the composition has a SEC Peak 4 area of 95 to 100%, no SEC Peak 3 area, and no SEC Peak 5 area of a total area of Peaks 1, 2, 3, 4, 5, and 6 in the SEC chromatogram.

14. The antiperspirant active composition of claim 1, wherein the SEC Peak 4 to Peak 3 intensity ratio is at least 17.

15. The antiperspirant active composition of claim 1, wherein the SEC Peak 4 to Peak 3 intensity ratio is at least 18.

16. The antiperspirant active composition of claim 1, wherein the SEC Peak 4 to Peak 3 intensity ratio is at least 19.

17. The antiperspirant active composition of claim 1, wherein the SEC Peak 4 to Peak 3 intensity ratio is at least 20.

18. The antiperspirant active composition of claim 1, wherein the SEC Peak 4 to Peak 3 intensity ratio is at least 30.

19. The antiperspirant active composition of claim 1, wherein the SEC Peak 4 to Peak 3 intensity ratio is at least 40.

20. The antiperspirant active composition of claim 1, wherein the SEC Peak 4 to Peak 3 intensity ratio is at least 50.

21. The antiperspirant active composition of claim 1, wherein the SEC Peak 4 to Peak 3 intensity ratio is at least 100.

22. An antiperspirant active composition comprising an aluminum chlorohydrate salt formed from at least one aluminum material chosen from aluminum chloride and a first aluminum chlorohydrate and an inorganic hydroxide base having an aluminum to chloride molar ratio of about 0.3:1 to about 3:1, exhibiting a SEC chromatogram having a SEC Peak 4 to Peak 3 intensity ratio of at least 16 and a Peak 4 intensity greater than a Peak 5 intensity in aqueous solution, and wherein the aluminum chlorohydrate salt has an OH to Al ratio of about 2:1 to about 2.6:1 based on the OH groups in the inorganic hydroxide base and the aluminum material.

23. The antiperspirant active of claim 22, wherein the aluminum chlorohydrate salt further comprises zirconium to form an aluminum-zirconium salt.

24. The antiperspirant active of claim 22, wherein the aluminum chlorohydrate salt is buffer free.

25. The antiperspirant active of claim 22 further comprising a buffer, wherein a molar ratio of buffer to aluminum is about 0.1:1 to about 3:1.

26. The antiperspirant active of claim 25, wherein the buffer is at least one buffer chosen from an amino acid, glycine, and betaine.

27. The antiperspirant active of claim 23, wherein a molar ratio of aluminum to zirconium is about 5:1 to about 10:1.

28. The antiperspirant active composition of claim 22, wherein the composition has a SEC Peak 4 area of 95 to 100% of a total area of Peaks 1, 2, 3, 4, 5, and 6 in the SEC chromatogram.

29. The antiperspirant active composition of claim 22, wherein the composition has a SEC Peak 3 area of less than 5% of a total area of Peaks 1, 2, 3, 4, 5, and 6 in the SEC chromatogram.

30. The antiperspirant active composition of claim 22, wherein the composition has no SEC Peak 3 area in the SEC chromatogram.

31. The antiperspirant active composition of claim 22, wherein the composition has a SEC Peak 5 area of less than 30% of a total area of Peaks 1, 2, 3, 4, 5, and 6 in the SEC chromatogram.

32. The antiperspirant active composition of claim 22, wherein the composition has no SEC Peak 5 area in the SEC chromatogram.

33. The antiperspirant active composition of claim 22, wherein the composition has a SEC Peak 1 area of less than 10% and a SEC Peak 2 area of less than 10% of a total area of Peaks 1, 2, 3, 4, 5, and 6 in the SEC chromatogram.

34. The antiperspirant active composition of claim 22, wherein the composition has a SEC Peak 4 area of 95 to 100%, no SEC Peak 3 area, and no SEC Peak 5 area of a total area of Peaks 1, 2, 3, 4, 5, and 6 in the SEC chromatogram.

35. The antiperspirant active composition of claim 22, wherein the SEC Peak 4 to Peak 3 intensity ratio is at least 17.

36. The antiperspirant active composition of claim 22, wherein the SEC Peak 4 to Peak 3 intensity ratio is at least 18.

37. The antiperspirant active composition of claim 22, wherein the SEC Peak 4 to Peak 3 intensity ratio is at least 19.

38. The antiperspirant active composition of claim 22, wherein the SEC Peak 4 to Peak 3 intensity ratio is at least 20.

39. The antiperspirant active composition of claim 22, wherein the SEC Peak 4 to Peak 3 intensity ratio is at least 30.

40. The antiperspirant active composition of claim 22, wherein the SEC Peak 4 to Peak 3 intensity ratio is at least 40.

41. The antiperspirant active composition of claim 22, wherein the SEC Peak 4 to Peak 3 intensity ratio is at least 50.

42. The antiperspirant active composition of claim 22, wherein the SEC Peak 4 to Peak 3 intensity ratio is at least 100.

* * * * *